United States Patent
Kawakami et al.

(10) Patent No.: US 10,426,784 B2
(45) Date of Patent: Oct. 1, 2019

(54) IMIDAZODIAZEPINE COMPOUND

(71) Applicant: Astellas Pharma Inc., Chuo-ku (JP)

(72) Inventors: Shimpei Kawakami, Tokyo (JP); Tomoyoshi Imaizumi, Tokyo (JP); Naoyuki Masuda, Tokyo (JP); Shigeki Kunikawa, Tokyo (JP); Masataka Morita, Tokyo (JP); Junko Yarimizu, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 15/737,564

(22) PCT Filed: Jun. 17, 2016

(86) PCT No.: PCT/JP2016/068080
§ 371 (c)(1),
(2) Date: Dec. 18, 2017

(87) PCT Pub. No.: WO2016/204268
PCT Pub. Date: Dec. 22, 2016

(65) Prior Publication Data
US 2018/0185383 A1    Jul. 5, 2018

(30) Foreign Application Priority Data

Jun. 19, 2015 (JP) .................... 2015-123478

(51) Int. Cl.
| | | |
|---|---|---|
| *C07D 498/00* | (2006.01) | |
| *A61K 31/551* | (2006.01) | |
| *A61K 31/5517* | (2006.01) | |
| *C07D 487/04* | (2006.01) | |
| *A61P 25/28* | (2006.01) | |
| *A61P 25/30* | (2006.01) | |
| *A61P 25/18* | (2006.01) | |
| *A61P 25/24* | (2006.01) | |
| *A61P 25/16* | (2006.01) | |

(52) U.S. Cl.
CPC ............ *A61K 31/551* (2013.01); *A61P 25/16* (2018.01); *A61P 25/18* (2018.01); *A61P 25/24* (2018.01); *A61P 25/28* (2018.01); *A61P 25/30* (2018.01); *C07D 487/04* (2013.01)

(58) Field of Classification Search
CPC . C07D 498/00; A61K 31/551; A61K 31/5517
See application file for complete search history.

(56) References Cited

U.S. PATENT DOCUMENTS

| | | | |
|---|---|---|---|
| 7,067,507 B2 * | 6/2006 | Pulley .................. | C07D 273/02 514/183 |
| 8,937,087 B2 | 1/2015 | Shiraki et al. | |
| 9,708,307 B2 | 7/2017 | Shiraki et al. | |
| 2007/0191447 A1 | 8/2007 | Kodo et al. | |
| 2007/0299118 A1 | 12/2007 | Starck et al. | |
| 2014/0315963 A1 | 10/2014 | Shiraki et al. | |

FOREIGN PATENT DOCUMENTS

| | | |
|---|---|---|
| WO | WO 03/077847 A2 | 9/2003 |
| WO | WO 2005/080334 A1 | 9/2005 |
| WO | WO 2005/118561 A1 | 12/2005 |
| WO | WO 2008/011551 A1 | 1/2008 |
| WO | WO 2014/171528 A1 | 10/2014 |

OTHER PUBLICATIONS

CADET. CNS and Neurological Disorders, 2010, 9, 526-38. (Year: 2010).*
STN Registry record of registry Nos. 2096375-86-7 and 2096236-93-8, accessed Oct. 30, 2018 (Year: 2018).*
International Search Report dated Aug. 2, 2016 in PCT/JP2016/068080 filed Jun. 17, 2016.
Written Opinion of the International Searching Authority dated Aug. 2, 2016 in PCT/JP2016/068080 filed Jun. 17, 2016 (with English translation), 8 pages.

* cited by examiner

*Primary Examiner* — Noble E Jarrell
(74) *Attorney, Agent, or Firm* — Oblon, McClelland, Maier & Neustadt, L.L.P.

(57) ABSTRACT

Compounds of formula (I) defined herein are useful as a dopamine D1 receptor positive allosteric modulators (D1 PAM) and can be used as an active ingredient of a pharmaceutical composition for preventing and/or treating cognitive impairment, schizophrenia negative symptom, CIAS, Parkinson's disease, Alzheimer's disease, Huntington's disease, depression, ADHD, drug dependency, or the like.

20 Claims, No Drawings

IMIDAZODIAZEPINE COMPOUND

TECHNICAL FIELD

The present invention relates to an imidazodiazepine compound which has a positive allosteric modulating action (hereinafter, referred to as PAM action) on a dopamine D1 receptor, and which is expected as an active ingredient of pharmaceutical compositions, particularly, pharmaceutical compositions for preventing and/or treating cognitive impairment, schizophrenia negative symptom, cognitive impairment associated with schizophrenia (CIAS), Parkinson's disease, Alzheimer's disease, Huntington's disease, depression, attention deficit hyperactivity disorder (ADHD), drug dependency, or the like.

BACKGROUND ART

Dopamine receptors belong among G-protein-coupled receptors that are expressed in the central nervous system. Dopamine receptors are classified into dopamine D1 receptor-like family and dopamine D2 receptor-like family. Among dopamine receptors, dopamine D1 and D5 receptors belong to the dopamine D1 receptor-like family, and dopamine D2, D3, and D4 receptors belong to the dopamine D2 receptor-like family.

It has been reported that the dopamine D1 receptor is coupled with Gs, which is a promoting G protein, to activate an adenylate cyclase, and enhances the production of cAMP in a cell to promote protein kinase A activity, and exhibit various functions (Medicinal Research Reviews, 2009, vol. 29(2), p. 272-294).

There is a report suggesting that the reduction of the dopamine D1 receptors in the prefrontal cortex plays an important role in cognitive impairment and schizophrenia negative symptom. Because in patients with schizophrenia, dopamine D1 receptors were significantly reduced in a part of the frontal lobe, called a prefrontal cortex. Furthermore, because the degree of reduction of the dopamine D1 receptors was correlated with the results of Wisconsin Card Sorting Test which is a test for the intensity of schizophrenia negative symptom and the function of the frontal lobe (Nature, 1997, vol. 385(6617), p. 634-636).

Even in patients with depression, similarly to patients with schizophrenia, functional impairment in the prefrontal cortex has been reported (Psychiatry Research, 1999, vol. 89, p. 171-187).

It has been reported that, in a cognitive impairment model, a dopamine D1 receptor agonist is useful (European Neuropsychopharmacology, 2009, vol. 19(6), p. 440-450; Psychopharmacology, 2010, vol. 210(3), p. 407-418; Molecular Pharmacology, 2007, vol. 71(6), p. 1598-1609; and Annals of the New York Academy of Sciences, 1996, vol. 777, p. 427-430).

It has been reported that a dopamine D1 receptor is related to schizophrenia negative symptom (The American Journal of Psychiatry, 2002, vol. 159(5), p. 761-767; and Pharmacopsychiatry, 2006, vol. 39(3), p. 115-116).

Therefore, the dopamine D1 receptor agonist is expected as a drug that stimulates the dopamine D1 receptor in the prefrontal cortex and can ameliorate cognitive impairment, schizophrenia negative symptom, CIAS, and depression.

There is a report suggesting that the dopamine D1 receptor agonist is expected to be applied to Parkinson's disease (Current Opinion in Investigational Drugs, 2001, vol. 2(11), p. 1582-1591) and Alzheimer's disease (The Journal of Biological Chemistry, 2011, vol. 286(5), p. 3270-3276).

Further, the dopamine D1 receptor agonist has been reported to exhibit the efficacy in each animal model of Huntington's disease (Neurodegenerative Diseases, 2011, vol. 8(4), p. 230-239) and drug dependency (Neuroscience Letters, 2012, vol. 513(2), p. 214-218).

Moreover, it has been suggested that a dopamine agonist is expected to be applied to cognitive impairment in ADHD (Neuropsychologia, 2013, vol. 51(2), p. 235-266; and Pharmacogenomics and Personalized Medicine, 2014, vol. 7, p. 349-356).

Therefore, a compound stimulating the dopamine D1 receptor is expected to be promising as an agent for preventing and/or treating diseases such as cognitive impairment, schizophrenia negative symptom, CIAS, Parkinson's disease, Alzheimer's disease, Huntington's disease, depression, ADHD, drug dependency, or the like.

The dopamine D1 receptor agonist is also used as an antihypertensive agent of peripherals (The New England Journal of Medicine, 2001, vol. 345(21), p. 1548-1557). Meanwhile, for example, it has been reported that dihydrexidine, which is a dopamine D1 receptor agonist that had been developed for Parkinson's disease, causes blood-pressure reduction as a side effect although exhibiting efficacy in Parkinson's disease (Clinical Neuropharmacology, 1998, vol. 21(6), p. 339-343).

Therefore, a compound that stimulates a dopamine D1 receptor but has no side effect, such as a blood-pressure reduction, is expected to be created.

A G-protein-coupled receptor has been long researched as an important target for drug discovery. In recent years, it has been revealed that many G-protein-coupled receptors also have allosteric sites different from orthosteric ligand sites (ACS Chemical Biology, 2008, vol. 3(9), p. 530-541). Here, research for drug discovery, in which allosteric sites in G-protein-coupled receptors are targets for drug discovery, has actively been made (British Journal of Pharmacology, 2012, vol. 165(6), p. 1659-1669).

A positive allosteric modulator (hereinafter, referred to as PAM) is a compound that binds to a site different from a binding site of an endogenous ligand to enhance a receptor function. PAM does not enhance a receptor function in itself, but enhances the receptor function in the presence of a ligand.

Therefore, it is expected that a dopamine D1 receptor PAM (hereinafter, referred to as D1 PAM) has a PAM action on a dopamine D1 receptor, can be used for preventing and/or treating cognitive impairment, schizophrenia negative symptom, CIAS, Parkinson's disease, Alzheimer's disease, Huntington's disease, depression, ADHD, drug dependency, or the like, and is useful as a drug with less side effects compared to a dopamine D1 receptor agonist.

It is reported in Patent Document 1 that a compound of the formula (A) has a benzodiazepine (03 receptor agonist action. In claims, an anti-anxiety agent or anti-depressant agent is described.

[Chem. 1]

(A)

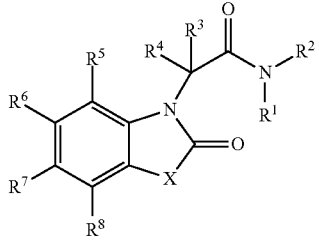

(In the formula, $R^1$ and $R^2$ form a saturated heterocyclic group which may be substituted together with a nitrogen atom to which they are bonded. However, (1) in the case of the following (a) or (b), $R^1$ and $R^2$ do not form a saturated heterocyclic group which may be substituted together with a nitrogen atom to which they are bonded. In (a), all of $R^5$, $R^6$, $R^7$, and R are hydrogen atoms. In (b), one or two of $R^5$, $R^6$, $R^7$, and $R^8$ are each independently halogen atoms, and the others are hydrogen atoms. X represents O, S, $NR^{10}$, or $CR^{11}R^{12}$. Refer to this publication for the other symbols.)

It is reported in Patent Document 2 that a compound of the formula (B) has urotensin II antagonist and inhibition actions, and is useful in congestive heart failure or the like.

[Chem. 2]

(B)

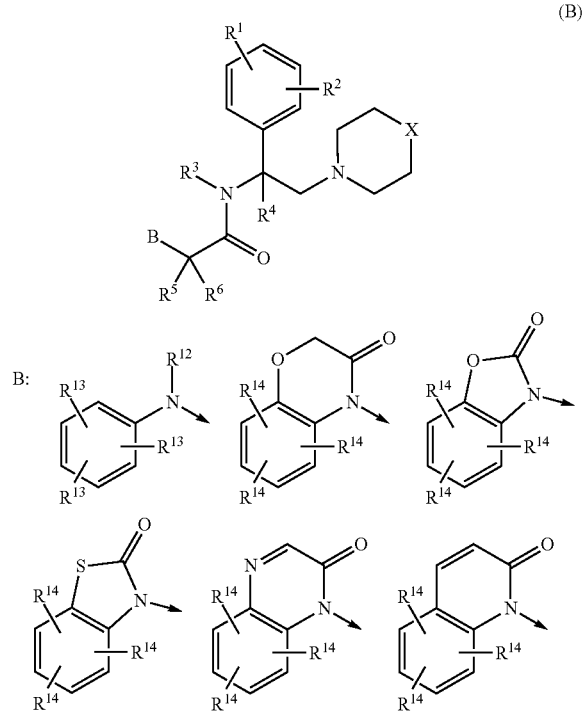

(Refer to this Publication for the Other Symbols.)

It is reported in Patent Document 3 that a compound of the formula (C) has cannabinoid 1 antagonist and/or inverse-agonist actions, and is useful as a central functional agent or the like.

[Chem. 3]

(C)

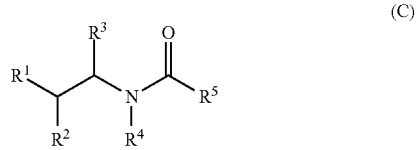

(In the formula, each of $R^1$ and $R^2$ is alkyl, cycloalkyl, aryl, aryl-alkyl, heteroaryl, heteoaryl-alkyl, or the like. Refer to this publication for the other symbols.)

It is reported in Patent Document 4 that a compound of the formula (D) is useful in the treatment and/or prevention of dyskinesia and/or movement fluctuation.

[Chem. 4]

(D)

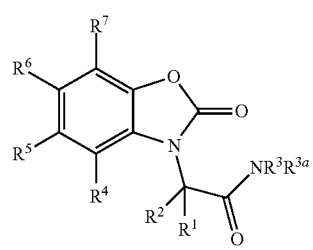

(In the formula, each of $R^3$ and $R^{3a}$ is H or unsubstituted $C_{1-4}$ alkyl. Refer to this publication for the other symbols.)

It is reported in Patent Document 5 that a compound of the formula (E) is useful in the treatment and/or prevention of schizophrenia.

[Chem. 5]

(E)

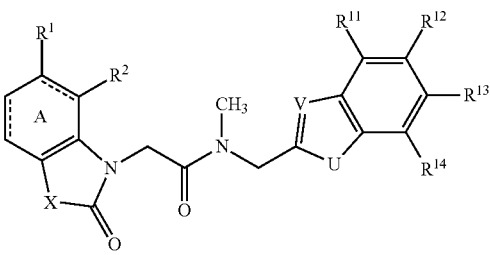

(Refer to this Publication for the Other Symbols.)

RELATED ART

Patent Document

Patent Document 1: WO 2005/080334
Patent Document 2: WO 2008/011551
Patent Document 3: WO 03/077847
Patent Document 4: WO 2005/118561
Patent Document 5: WO 2014/171528

DISCLOSURE OF INVENTION

Problems to be Solved by the Invention

There is provided a compound which has a PAM action on a dopamine D1 receptor, and which is expected to be an active ingredient of pharmaceutical compositions, particularly, pharmaceutical compositions for preventing and/or treating cognitive impairment, schizophrenia negative symptom, CIAS, Parkinson's disease, Alzheimer's disease, Huntington's disease, depression, ADHD, or drug dependency.

Means for Solving the Problems

The present inventors have intensively studied a compound having a PAM action on a dopamine D1 receptor. As a result, they have found that the imidazodiazepine compound of the present invention has a PAM action on a dopamine D1 receptor, thereby completing the present invention.

That is, the present invention relates to a compound of the formula (I) or a salt thereof, as well as a pharmaceutical composition comprising a compound of the formula (I) or a salt thereof and an excipient:

[Chem. 6]

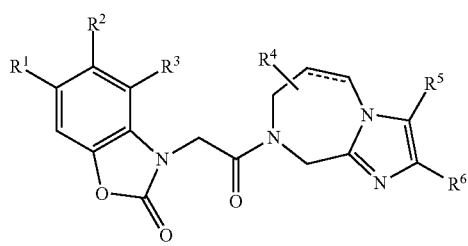

(I)

(in the formula,
$R^1$, $R^2$, and $R^3$ are the same as or different from each other, and are H, halogen, lower alkyl, or halo-lower alkyl;
$R^4$ is H, halogen, lower alkyl, or halo-lower alkyl;
$R^5$ is H;
$R^6$ is phenyl which may be substituted; or
$R^5$ and $R^6$ may form a benzene ring which may be substituted, together with carbon atoms to which they are bonded; and
═══ is a single bond or a double bond.)

In addition, unless otherwise specified, when symbols in a certain chemical formula in the present specification are also used in another chemical formula, the same symbol represents the same meaning.

Further, the present invention relates to a pharmaceutical composition for preventing and/or treating cognitive impairment, schizophrenia negative symptom, CIAS, Parkinson's disease, Alzheimer's disease, Huntington's disease, depression, ADHD, or drug dependency, which comprises a compound of the formula (I) or a salt thereof.

Further, said pharmaceutical composition includes an agent for preventing and/or treating cognitive impairment, schizophrenia negative symptom, CIAS, Parkinson's disease, Alzheimer's disease, Huntington's disease, depression, ADHD, or drug dependency, which comprises a compound of the formula (I) or a salt thereof.

Furthermore, the present invention relates to:
(1) use of a compound of the formula (I) or a salt thereof, for the manufacture of a pharmaceutical composition for preventing and/or treating cognitive impairment, schizophrenia negative symptom, CIAS, Parkinson's disease, Alzheimer's disease, Huntington's disease, depression, ADHD, or drug dependency;

(2) use of a compound of the formula (I) or a salt thereof, for preventing and/or treating cognitive impairment, schizophrenia negative symptom, CIAS, Parkinson's disease, Alzheimer's disease, Huntington's disease, depression, ADHD, or drug dependency;
(3) a compound of the formula (I) or a salt thereof, for preventing and/or treating cognitive impairment, schizophrenia negative symptom, CIAS, Parkinson's disease, Alzheimer's disease, Huntington's disease, depression, ADHD, or drug dependency; and
(4) a method for preventing and/or treating cognitive impairment, schizophrenia negative symptom, CIAS, Parkinson's disease, Alzheimer's disease, Huntington's disease, depression, ADHD, or drug dependency, which comprises administering an effective amount of a compound of the formula (I) or a salt thereof to a subject.

Here, the "subject" refers to a human or other animal in need of such prevention or treatment, and, in a certain embodiment, a human in need of such prevention or treatment.

Effects of the Invention

The compound of the formula (I) or a salt thereof has a PAM action on a dopamine D1 receptor, and can be used as an agent for preventing and/or treating cognitive impairment, schizophrenia negative symptom, CIAS, Parkinson's disease, Alzheimer's disease, Huntington's disease, depression, ADHD, or drug dependency.

EMBODIMENTS FOR CARRYING OUT THE INVENTION

Hereinafter, the present invention will be described in detail.

The "alkyl" and "alkylene" both mean a linear or branched saturated hydrocarbon chain, and mean a monovalent group and a divalent group, respectively.

The "lower alkyl" is alkyl having 1 to 6 carbon atoms (hereinafter, referred to as $C_{1-6}$), for example, methyl, ethyl, n-propyl, isopropyl, n-butyl, isobutyl, sec-butyl, tert-butyl, n-pentyl, n-hexyl, or the like; in one embodiment, $C_{1-4}$ alkyl; in one embodiment, methyl or ethyl; and in one embodiment, methyl.

The "lower alkylene" is $C_{1-6}$ alkylene, for example, methylene, ethylene, trimethylene, tetramethylene, pentamethylene, hexamethylene, propylene, methylmethylene, ethylethylene, 1,2-dimethylethylene, 2,2-dimethylethylene, 1,1,2,2-tetramethylethylene, or the like; in one embodiment, $C_{1-4}$ alkylene; in one embodiment ethylene or 2,2-dimethylethylene; and in one embodiment, ethylene.

The "halogen" means F, Cl, Br, or I.

The "halo-lower alkyl" is $C_{1-6}$ alkyl substituted with one or more halogen atoms; in one embodiment, $C_{1-6}$ alkyl substituted with one to five halogen atoms; and in one embodiment, $CF_3$.

In the present specification, the term "may be substituted" means that it is unsubstituted or has one to four substituents; and in one embodiment, it is unsubstituted or has one to three substituents. In the case of having a plurality of substituents, these substituents may be the same as or different from each other.

In the term "phenyl which may be substituted" in $R^6$, the substituent includes $R^{41}$ in one embodiment, and $R^{42}$ in one embodiment. $R^{41}$ is a group selected from the group consisting of —OH, —O-lower alkyl, —CN, halogen, lower alkyl, halo-lower alkyl, lower alkylene-O-lower alkyl, —C(=O)-lower alkyl, and —C(=O)-lower alkylene-CN. $R^{A2}$ is a group selected from the group consisting of halogen, lower alkyl, and halo-lower alkyl.

In the term "may form a benzene ring which may be substituted, together with carbon atoms to which they are bonded" in $R^5$ and $R^6$, the substituent includes $R^{B1}$ in one embodiment, and $R^{B2}$ in one embodiment. $R^{B1}$ is a group selected from the group consisting of —OH, —O-lower alkyl, —CN, halogen, lower alkyl, halo-lower alkyl, lower alkylene-O-lower alkyl, —C(=O)-lower alkyl, and —C(=O)-lower alkylene-CN. $R^{B2}$ is a group selected from the group consisting of halogen, lower alkyl, and halo-lower alkyl.

Embodiments of the present invention are set forth below.

(1) In one embodiment, a compound of the formula (I) or a salt thereof, in which $R^1$, $R^2$, and $R^3$ are the same as or different from each other, and are H or halogen.

(2) In one embodiment, a compound of the formula (I) or a salt thereof, in which $R^1$ is H.

(3) In one embodiment, a compound of the formula (I) or a salt thereof, in which $R^2$ is H or halogen; or in one embodiment, a compound of the formula (I) or a salt thereof, in which $R^2$ is H, F, or Cl; or in one embodiment, a compound of the formula (I) or a salt thereof, in which $R^2$ is H.

(4) In one embodiment, a compound of the formula (I) or a salt thereof, in which $R^3$ is H or halogen; or in one embodiment, a compound of the formula (I) or a salt thereof, in which $R^3$ is H or F; or in one embodiment, a compound of the formula (I) or a salt thereof, in which $R^3$ is halogen.

(5) In one embodiment, a compound of the formula (I) or a salt thereof, in which $R^4$ is H or halogen; or in one embodiment, a compound of the formula (I) or a salt thereof, in which $R^4$ is H or F; or in one embodiment, a compound of the formula (I) or a salt thereof, in which $R^4$ is H.

(6) In one embodiment, a compound of the formula (I) or a salt thereof, in which $R^5$ is H.

(7) In one embodiment, a compound of the formula (I) or a salt thereof, in which $R^6$ is phenyl which may be substituted with one to four $R^{A1}$'s which are the same as or different from each other; or in one embodiment, a compound of the formula (I) or a salt thereof, in which $R^6$ is phenyl which may be substituted with one $R^{A2}$; or in one embodiment, a compound of the formula (I) or a salt thereof, in which $R^6$ is phenyl which may be substituted with one $R^{A2}$ at a para-position from its bond.

(8) In one embodiment, a compound of the formula (I) or a salt thereof, in which $R^5$ and $R^6$ may form, together with carbon atoms to which they are bonded, a benzene ring which may be substituted with one to four $R^{B1}$'s which are the same as or different from each other.

(9) In one embodiment, a compound of the formula (I) or a salt thereof, in which = is a single bond.

(10) A compound of the formula (I) or a salt thereof, which is a consistent combination of two or more of the groups described in the above (1) to (9).

Examples of the compound which is a combination of embodiments as in the above (10) are exemplified as follows.

(11) In one embodiment, a compound of the formula (I) or a salt thereof, in which $R^1$ is H, $R^2$ is H or halogen, $R^3$ is halogen, $R^4$ is H, and = is a single bond.

(12) In one embodiment, a compound of the formula (I) or a salt thereof, in which $R^1$ is H, $R^2$ is H or halogen, $R^3$ is halogen, $R^4$ is H, $R^5$ is H, $R^6$ is phenyl which may be substituted, and = is a single bond.

(13) In one embodiment, a compound of the formula (I) or a salt thereof, in which $R^1$ is H, $R^2$ is H, $R^3$ is halogen, $R^4$ is H, $R^5$ is H, $R^6$ is phenyl which may be substituted with one to four $R^{A1}$'s which are the same as or different from each other, and = is a single bond.

(14) In one embodiment, a compound of the formula (I) or a salt thereof, in which $R^1$ is H, $R^2$ is H or halogen, $R^3$ is halogen, $R^4$ is H, $R^5$ and $R^6$ may form a benzene ring which may be substituted, together with carbon atoms to which they are bonded, and = is a single bond.

(15) In one embodiment, a compound of the formula (I) or a salt thereof, in which $R^1$ is H, $R^2$ is halogen, $R^3$ is halogen, $R^4$ is H, $R^5$ and $R^6$ may form, together with carbon atoms to which they are bonded, a benzene ring which may be substituted with one to four $R^{B1}$'s which are the same as or different from each other, and = is a single bond.

(16) In one embodiment, a compound of the formula (I) or a salt thereof, in which $R^5$ is H, and $R^6$ is phenyl which may be substituted.

(17) In one embodiment, the compound or a salt thereof according to (16), in which = is a single bond.

(18) In one embodiment, the compound or a salt thereof according to (17), in which $R^4$ is H.

(19) In one embodiment, the compound or a salt thereof according to (18), in which $R^1$ is H, $R^2$ is H or halogen, and $R^3$ is halogen.

(20) In one embodiment, the compound or a salt thereof according to (19), in which $R^6$ is phenyl which may be substituted with one to four $R^{A1}$'s which are the same as or different from each other, and $R^{A1}$ is a group selected from the group consisting of —OH, —O-lower alkyl, —CN, halogen, lower alkyl, halo-lower alkyl, lower alkylene-O-lower alkyl, —C(=O)-lower alkyl, and —C(=O)-lower alkylene-CN.

(21) In one embodiment, the compound or a salt thereof according to (20), in which $R^6$ is phenyl which may be substituted with one $R^{A2}$, and $R^{A2}$ is a group selected from the group consisting of halogen, lower alkyl, and halo-lower alkyl.

(22) In one embodiment, the compound or a salt thereof according to (21), in which $R^2$ is H.

(23) In one embodiment, the compound or a salt thereof according to (22), in which $R^6$ is phenyl which may be substituted with one $R^{A2}$ at a para-position from its bond.

Examples of specific compounds encompassed by the present invention include the following compounds and salts thereof.

4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one, 4-fluoro-3-{2-[2-(2-fluorophenyl)-6,7-dihydro-5H-imidazo[1,2-a][1,4]diazepin-8(9H)-yl]-2-oxoethyl}-1,3-benzoxazol-2(3H)-one, 3-[2-(4,5-dihydro-1H-[1,4]diazepino[1,2-a]benzimidazol-2(3H)-yl)-2-oxoethyl]-4,5-difluoro-1,3-benzoxazol-2(3H)-one, 4-fluoro-3-[2-(8-fluoro-4,5-dihydro-1H-[1,4]diazepino[1,2-a]benzimidazol-2(3H)-yl)-2-oxoethyl]-1,3-benzoxazol-2(3H)-one, 4,5-difluoro-3-[2-oxo-2-(2-phenyl-6,7-dihydro-5H-imidazo[1,2-a][1,4]diazepin-8(9H)-yl)ethyl]-1,3-benzoxazol-2(3H)-one, 4-fluoro-3-{2-[2-(3-fluorophenyl)-6,7-dihydro-5H-imidazo[1,2-a][1,4]diazepine-8(9H)-yl]-2-oxoethyl}-1,3-benzoxazol-2(3H)-one, and 3-{2-[2-(4-chlorophenyl)-6,7-dihydro-5H-imidazo[1,2-a][1,4]diazepin-8(9H)-yl]-2-oxoethyl}-4-fluoro-1,3-benzoxazol-2(3H)-one.

In the compound of the formula (I), a tautomer can exist depending on the kind of substituents. In the present specification, the compound of the formula (I) is described in only a form of isomers, but, the present invention includes other isomers, and also includes compounds from which isomers are separated, or mixtures thereof.

Further, there is a case of the compound of the formula (I) having asymmetric carbon atoms. Based on this case, optical isomers exist in the compound of the formula (I). In the present invention, the compound of the formula (I) also includes compounds from which optical isomers are separated, or mixtures thereof.

Further, the present invention includes a pharmaceutically acceptable prodrug of the compound of the formula (I). The pharmaceutically acceptable prodrug is a compound having a group that can be converted into an amino group, a hydroxyl group, a carboxyl group, or the like by solvolysis or under physiological conditions. As the group forming a prodrug, for example, there is a group described in Progress in Medicine, 1985, vol. 5, p. 2157-2161 or "Pharmaceutical Research and Development" (Hirokawa Publishing Company), 1990, vol. 7 (Drug Design), p. 163-198.

Further, the salt of the compound of the formula (I) is a pharmaceutically acceptable salt of the compound of the formula (I), and there is a case of forming an acid addition salt or a salt with base depending on the kind of substituents. Specific examples thereof include acid addition salts with inorganic acids, such as hydrochloric acid, hydrobromic acid, hydroiodic acid, sulfuric acid, nitric acid, and phosphoric acid, and acid addition salts with organic acids, such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric tartaric acid, citric acid, methane sulfonic acid, ethane sulfonic acid, benzene sulfonic acid, p-toluene sulfonic acid, aspartic acid, and glutamic acid; salts with alkali metals, such as sodium or potassium; salts with alkali earth metals, such as calcium and magnesium; salts with metals, such as aluminum; salts with organic bases, such as methylamine, ethylamine, ethanolamine, lysine, and ornithine; salts with various amino acids, such as acetyl leucine, and amino derivatives; and ammonium salts.

Further, the present invention also includes various hydrates, solvates and crystalline polymorphic substances of the compound of the formula (I) and salt thereof. Moreover, the present invention also includes compounds labeled with various radioactive or non-radioactive isotopes.

The "positive allosteric modulating action (PAM action)" means an action of enhancing a receptor function by binding to a site other than a site to which an endogenous ligand binds with respect to a receptor.

The "positive allosteric modulator (PAM)" means a compound having the PAM action. For example, in Test Example 1, the PAM means a compound shifting a dopamine dose response curve leftward.

The PAM does not enhance the receptor function in itself, but enhances the receptor function in the presence of a ligand.

The disease names in the present specification refer to International Disease Classification "ICD10" of World Health Organization (WHO), 5$^{th}$ edition of the Diagnostic and Statistical Manual (DSM-5) of Mental Disorders in American Psychiatric Association (APA), and/or Societas Neurologica Japonica.

The "schizophrenia" is a disease characterized by impairment of various mental functions, such as cognition, emotion, motivation, behavior, and self-consciousness. Its symptoms are classified into positive and negative symptoms and cognitive impairment. The positive symptom, for example, is a symptom, such as hallucination, delusion, or the like. The negative symptom, for example, is social withdrawal or flattening of emotion.

The "Schizophrenia negative symptom" is a negative symptom in schizophrenia.

The "cognitive impairment associated with schizophrenia (CIAS)" is cognitive impairment associated with schizophrenia.

(Preparation Method)

The compound of the formula (I) and salt thereof can be prepared by applying various known synthesis methods using the characteristics based on the kind of its basic structure or substituent. At this time, there is a technically effective case in manufacturing technology that, according to the kind of a functional group, the functional group is replaced with a suitable protective group (group that can be easily converted into the functional group) in the step from a starting material to an intermediate. As the protective group, for example, there are exemplified protective groups described in "Greene's Protective Groups in Organic Synthesis", written by Peter G M. Wuts and Theodora W. Greene, fourth edition, 2006. These protective groups may be selected and used depending on the reaction conditions thereof. In this method, after the reaction was carried out by introducing the protective group, if necessary, a desired compound can be obtained by removing the protective group.

Further, the prodrug of the compound of the formula (I), similarly to the above protective group, can be prepared by introducing a specific group or by further performing a reaction using the obtained compound of the formula (I) in the step from a starting material to an intermediate. The reaction can be performed by applying a method known to those skilled in the art, such as general esterification, amidation, dehydration, or the like.

Hereinafter, typical preparation methods of the compound of the formula (I) will be described. Each of the preparation methods can also be carried out with reference to References appended in the corresponding description. The preparation method of the present invention is not limited to Examples shown below.

In the present specification, the following abbreviations are used.

DMF=N,N-dimethylformamide, DMSO=dimethyl sulfoxide, EtOAc=ethyl acetate, EtOH=ethanol, Hex=hexane, MeCN=acetonitrile, MeOH=methanol, THF=tetrahydrofuran.

nBuLi=n-butyl lithium, CDI=1,1'-carbonyl bis(1H-imidazole), DCC=N,N'-dicyclohexyl carbodiimide, DBU=1,8-diazabicyclo[5.4.0]undeca-7-ene, DIPEA=N,N-diisopropylethylamine, DMAP=N,N-dimethyl-4-aminopyridine, DPPA=diphenylphosphoryl azide, HATU=O-(7-azabenzotriazol-1-yl)-N,N,N',N'-tetramethyluronium hexafluorophosphate, HOBt=1-hydroxybenzotriazole, KOtBu=potassium tert-butoxide, NaOtBu=sodium tert-butoxide, NMM=N-methylmorpholine, NMP=N-methyl-2-pyrrolidone, Pd/C=palladium on carbon, PPh$_3$=triphenylphosphine, Pd2dba3=tris(dibenzylidene acetone) dipalladium(0), TBAB=tetrabutylammonium bromide, TEA=triethylamine, TFA=trifluoroacetic acid, WSC=N-[3-(dimethylamino)propyl]-N'-ethylcarbodiimide, WSC.HCl=N-[3-(dimethylamino)propyl]-N'-ethylcarbodiimide hydrochloride, xantphos=9,9'-dimethyl-4,5-bis(diphenylphosphino) xanthene.

Silica gel CC=silica gel column chromatography.

Brine=saturated NaCl aqueous solution, saturated aqueous sodium bicarbonate=saturated $NaHCO_3$ aqueous solution, $MgSO_4$=anhydrous magnesium sulfate, $Na_2SO_4$=anhydrous sodium sulfate.

In structural formulae and groups in the present specification, the following abbreviations are used.

Ac=acetyl, BOC=tert-butoxycarbonyl, t-Bu=tert-butyl, Et=ethyl, Halo=halogen, Me=methyl, MsO=methanesulfonyloxy, MOM=methoxymethyl, TBDMS=tert-butyldimethylsilyl, TsO=p-toluenesulfonyloxy.

(First Preparation Method)

[Chem. 7]

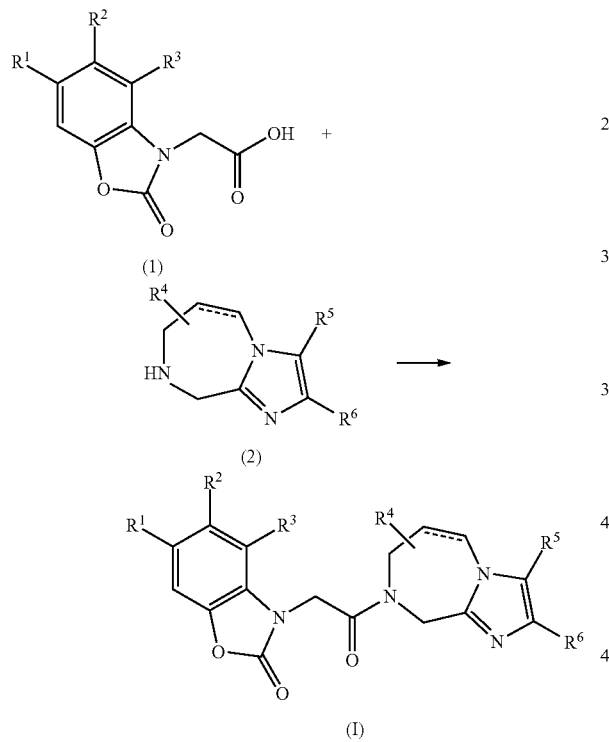

The compound of the formula (I) can be prepared from a compound (1) and a compound (2).

In this reaction, the compound (1) and the compound (2) are used in equivalent amounts or either thereof in an excess amount, and the mixture thereof is generally stirred in a solvent inert to the reaction in the presence of a condensing agent for 0.1 hours to 5 days under cooling to heating, preferably at −20° C. to 60° C. Examples of the solvent include aromatic hydrocarbons, such as toluene or the like; halogenated hydrocarbons, such as dichloromethane or the like; ethers, such as THF or the like; DMF; NMP; DMSO; EtOAc; MeCN; water; and mixtures thereof. Examples of the condensing agent include HATU, WSC, WSC.IICl, DCC, CDI, DPPA, and the like. There is a case that the use of an additive (for example, HOBt) is preferable for the reaction. There is a case that this reaction is further smoothly performed by the presence of an organic base, such as TEA, DIPEA, NMM, or the like, or an inorganic base, such as $K_2CO_3$, $Na_2CO_3$, KOH, or the like.

Further, a method of converting the compound (1) into a reactive derivative and then reacting the reactive derivative with the compound (2) can be used. Examples of the reactive derivative of carboxylic acid include acid halides obtained by the reaction with a halogenating agent, such as $POCl_3$, $SOCl_2$, $(COCl)_2$, or the like; mixed acid anhydrides obtained by the reaction with isobutyl chloroformate and the like; and active esters obtained by the condensation with HOBt and the like. If a small amount of DMF is used as an additive in the synthesis of acid halide, the reaction proceeds more easily. As the additive, a base, such as DMAP, can be used. The reaction of the reactive derivative with the compound (2) can be performed in a solvent inert to the reaction, such as halogenated hydrocarbons, aromatic hydrocarbons, or ethers under cooling to heating, preferably at −78° C. to 60° C.

[Literature] "Organic Functional Group Preparations", written by SR Sandler and W. Karo al., second edition, vol. 1, Academic Press Inc., 1991; "Courses in Experimental Chemistry (fifth edition)", edited by Japan Chemical Society, vol. 16, 2005, Maruzen.

(Second Preparation Method)

[Chem. 8]

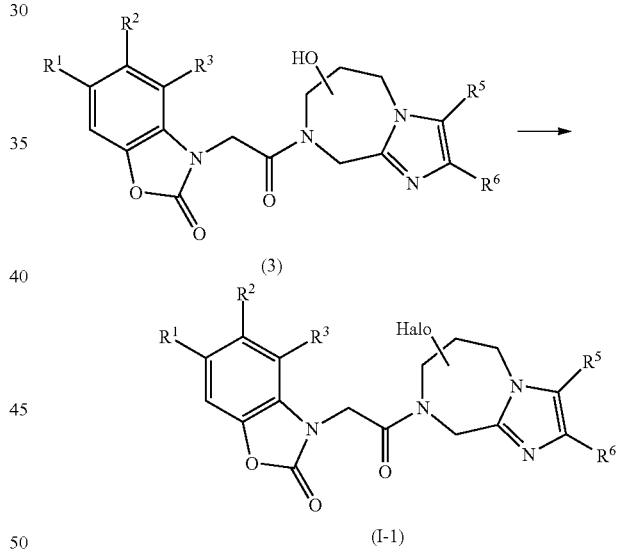

(In the formula, Halo represents a halogen. The same shall apply hereinafter.)

A compound (I-1) can be prepared from a compound (3).

This reaction is a halogenation of a hydroxyl group. In a solvent inert to the reaction, $PPh_3$ and a halogen source are added to the compound (3), followed by stirring for 0.5 hours to 8 hours at 20° C. to 100° C. As the solvent, for example, an ether-based solvent, such as THF or the like, is exemplified. Examples of the halogen source include bis(2-methoxyethyl) aminosulfur trifluoride, $CCl_4$, $CBr_4$, and $I_2$. Here, the chlorination using $PPh_3$ and $CCl_4$ is a so-called Appel reaction.

[Literature] Angewandte Chemie International Edition, p. 801, vol. 14, 1975.

(Starting Material Preparation Method 1)

[Chem. 9]

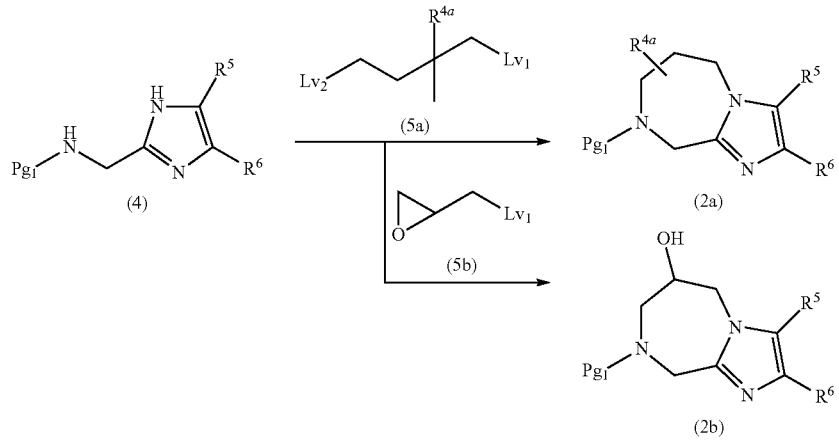

(In the formulae, $R^{4a}$ represents H, halogen, lower alkyl, halo-lower alkyl, or —O-lower alkyl. As shown in the formula (5a), $R^{4a}$ may be substituted to any carbon atom of a propylene chain. $Pg_1$ represents a protective group. Each of $Lv_1$ and $Lv_2$ represents a leaving group. The same shall apply hereinafter.)

A starting compound (2a) can be prepared from a compound (4) and a compound (5a). A starting compound (2b) can be prepared from a compound (4) and a compound (5b). Examples of the leaving group include Hal (hereinafter, Hal represents as Cl, Br, or I), an MsO group, a TsO group, and the like. Examples of $Pg_1$ include a benzyl group and a BOC group.

In this reaction, the compound (4) and the compound (5a) are used equivalent amounts or either thereof in an excess amount, and the mixture thereof is generally stirred in a solvent inert to the reaction or without solvent for 0.1 hours to 5 days under cooling to under heating to reflux, preferably at 0° C. to 80° C. Examples of the solvent include aromatic hydrocarbons, ethers, halogenated hydrocarbons, DMF, DMSO, EtOAc, MeCN, and mixtures thereof. There is a case that this reaction is further smoothly performed by the presence of an organic base, such as TEA, DIPEA, NMM, or the like, or an inorganic base, such as KOtBu, $K_2CO_3$, $Na_2CO_3$, NaOH, or the like.

[Literature] "Organic Functional Group Preparations", written by SR Sandler and W. Karo, second edition, vol. 1, Academic Press Inc., 1991; "Courses in Experimental Chemistry", fifth edition, edited by Japan Chemical Society, vol. 14, 2005, Maruzen.

(Starting Material Preparation Method 2)

[Chem. 10]

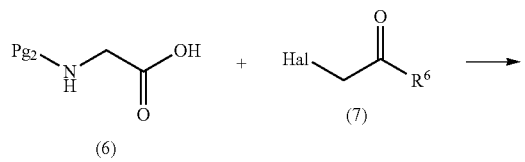

-continued

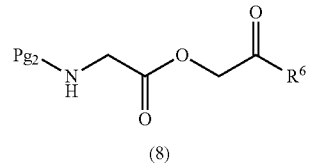

(In the formula, Hal represents Cl, Br, or I. $Pg_2$ represents a protective group. The same shall apply hereinafter.)

A compound (8) can be prepared from a compound (6) and a compound (7). As $Pg_2$, BOC or the like is exemplified.

This reaction can be performed in the same method as in the starting material preparation method 1. The compound (6) is added to the compound (7) in a solvent inert to the reaction, followed by stirring for 1 hour to 2 days at room temperature or higher in the presence of a base. As the base, an inorganic base is used, and examples thereof include $K_2CO_3$, $Na_2CO_3$, $Cs_2CO_3$, KOH, and the like. As the solvent, MeCN or the like is exemplified.

[Chem. 11]

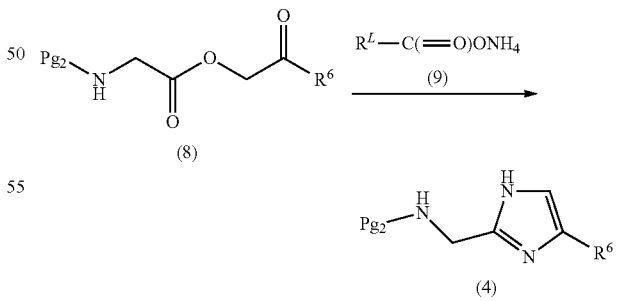

(In the formula, $R^L$ represents lower alkyl. The same shall apply hereinafter.)

A compound (4) can be prepared from a compound (8) and a compound (9).

In this reaction, the compound (8) and the compound (9) are stirred in a solvent inert to the reaction for 12 hours to 3 days at 100° C. or higher or under a reflux condition. Examples of the solvent include aromatic hydrocarbons, such as toluene or the like.

(Starting Material Preparation Method 3)

[Chem. 12]

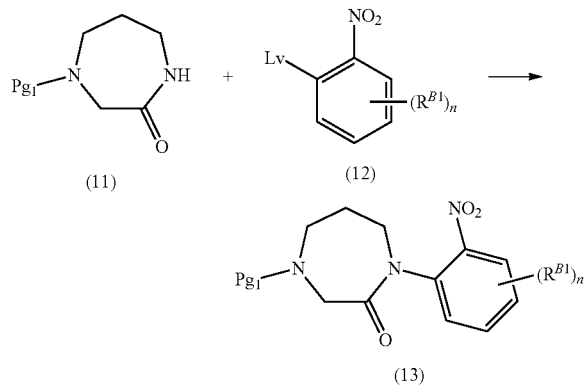

(In the formula, Lv represents a leaving group. n represents an integer of 1 to 4. The same shall apply hereinafter.)

A compound (13) can be prepared from a compound (11) and a compound (12).

The leaving group Lv, for example, is halogen or —OSO$_2$CF$_3$.

In this reaction, a metal, such as palladium or the like, and a ligand, such as PPh$_3$ or the like, are added to the compound (11) and the compound (12) as a catalyst in the presence of a base in a solvent inert to the reaction, followed by stirring for 5 hours to 4 days at 20° C. to 140° C. Examples of the catalyst include Pd2dba3 and the like. Examples of the base include bis(trimethylsilyl)sodium amide, NaOtBu and the like. Examples of the solvent include dioxane and the like. This is so-called Buchwald-Hartwig Cross Coupling.

[Literature] Journal of the American Chemical Society, p. 5969, vol. 116, 1994; Journal of the American Chemical Society, p. 7901, vol. 116, 1994; Angewandte Chemie International Edition, p. 1348, vol. 34, 1995; Tetrahedron Letters, p. 3609, vol. 36, 1995.

[Chem. 13]

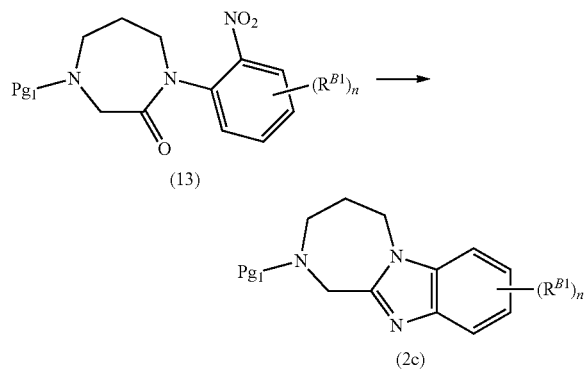

A compound (2c) is prepared by the reduction of a compound (13).

This reaction is a general method of reducing a nitro group. In this reaction, iron, tin, or the like is added to the compound (13) in a solvent, such as hydrochloric acid, acetic acid, or the like, followed by stirring for 0.5 hours to 3 days at 50° C. to 140° C.

(Starting Material Preparation Method 4)

[Chem. 14]

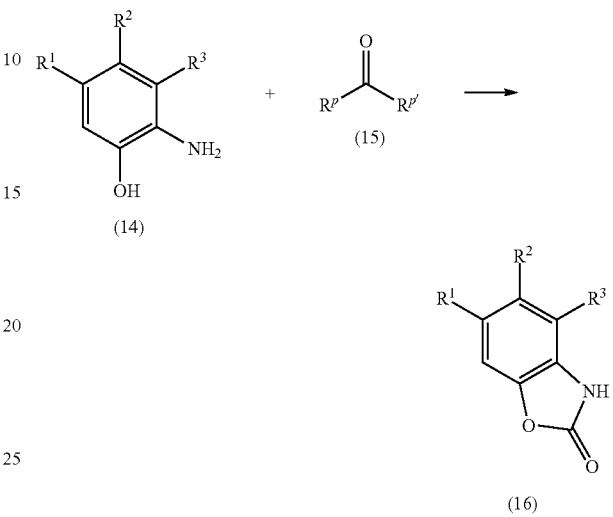

(In the formula, (R$^p$, R$^{p'}$) represents a combination of (imidazolyl, imidazolyl), (Cl$_3$C—O—, —O—CCl$_3$), (Cl, —O—CCl$_3$) (Cl, —O-phenyl), (Cl, —O-paranitrophenyl).)

A compound (16) can be prepared from a compound (14) and a compound (15).

In this reaction, the compound (14) is added to an equivalent amount or an excess amount of the compound (15) in a solvent inert to the reaction, and, preferably, the mixture thereof is stirred for 0.1 hours to 1 day under cooling to under heating, preferably at 50° C. to 150° C. Examples of the solvent include halogenated hydrocarbons, aromatic hydrocarbons, ethers, DMF, DMSO, EtOAc, MeCN, and mixed solvents thereof. The compound (15) is also known as a carbonyl reagent, and examples thereof include 4-nitrophenyl chloroformate and phenyl chloroformate as well as CDI, diphosgene, and triphosgene. In the case where a phenyl carbonate form, which is an intermediate, is stable (for example, in the case where 4-nitrophenyl chloroformate or phenyl chloroformate is used), this intermediate is once isolated, and the reaction can be carried out again.

[Literature] "Organic Functional Group Preparations", written by S. R. Sandler and W. Karo, second edition, Academic Press Inc., vol. 2, 1991.

[Chem. 15]

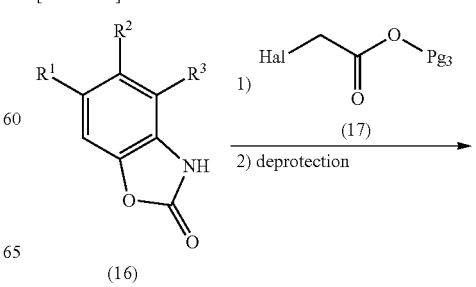

-continued

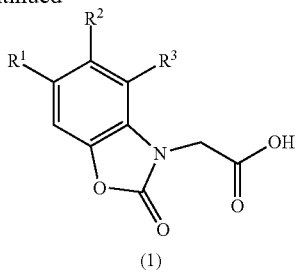

(In the formula, Pg₃ represents a protective group. The same shall apply hereinafter.)

A compound (1) can be prepared from a compound (16) and a compound (17).

A Pg₃ ester form of the compound (1) can be prepared from the compound (16) and the compound (17). As the leaving group, for example, an MsO group, a TsO group, or the like can be used in addition to Hal. Examples of the protective group Pg₃ include a Me group, an Et group, a tBu group, and the like.

In this reaction, the compound (16) and the compound (17) are used in equivalent amounts or either thereof in an excess amount, and the mixture thereof is stirred in the presence of a base. As the solvent, MeCN or the like is exemplified. There is a case that the reaction proceeds more smoothly by a phase-transfer catalyst, such as TBAB or the like.

The compound (1) is prepared by deprotecting Pg₃ from the obtained Pg₃ ester for of the compound (1). The deprotection can be performed with reference to "Greene's Protective Groups in Organic Synthesis", written by Peter G. M. Wuts and Theodora W. Greene, fourth edition, 2006.

The compound of the formula (I) is purified by isolating a free compound or a salt thereof, a hydrate, a solvate, or a crystalline polymorphic substance. The salt of the compound of the formula (I) can also be prepared by a general salt formation reaction.

The isolation and purification can be performed by applying general chemical operations, such as extraction, fractional crystallization, and various types of fractional chromatography.

Various isomers can be prepared by selecting a suitable starting compound, or can be separated by using the difference in physicochemical properties between the isomers. For example, optical isomers can be obtained by a general optical resolution method of a racemic compound (for example, fractional crystallization of a diastereomeric salt with an optically active base or acid, or chromatography using a chiral column), and can be prepared from a suitable optically active starting compound.

In the powder X-ray diffraction pattern described in the present specification, in the identity certification of crystals, due to the nature of data, crystal lattice intervals and the entire pattern are important, and in the diffraction angle and diffraction intensity thereof, some errors may occur depending on direction of crystal growth, particle size, and measurement conditions. Therefore, strict interpretation should not be required. In the present specification, the diffraction angle (2θ(°)) in the powder X-ray diffraction pattern is interpreted in consideration of a generally acceptable error range in the corresponding measurement method, and can take an error range of ±0.2°, in an aspect. Further, for example, in the case where measurement is performed in a state of a mixture with an excipient, in the peak located on the slope of a base line existing in the vicinity of the peak derived from the excipient, apparently, there may be a case where the peak is shifted by about ±0.30.

The pharmacological activity of the compound of the formula (I) was evaluated by the following tests.

Abbreviations

In the present specification, particularly, in Test Examples, the following abbreviations are used.

ATCC=American Type Culture Collection, CHO cell=Chinese hamster ovary cell, FBS=fetal bovine serum, IBMX=3-isobutyl-1-methylxanthine, MTX=methotrexate, αMEM=alpha modified Eagle's minimum essential medium containing ribonucleoside and deoxynucleoside-free L-glutamine, TR-FRET=Time-resolved fluorescence resonance energy transfer, NMDA=N-methyl-D-aspartic acid, PCP=phencyclidine, WCST=Wisconsin Card Sorting Test. SD2=simple discrimination 2, CD=compound discrimination, ID=Intradimensional-shift, IDR=ID-shift reversal, ED=extradimensional-shift, EDR=extradimensional-shift reversal, CIAS=cognitive impairment associated with schizophrenia, ADHD=attention deficit hyperactivity disorder.

(Material)

The composition of a buffer solution used in Test Example 1 is described.

Buffer solution for assay=αMEM containing 1 mM IBMX

Buffer solution for dilution=αMEM containing 1 mM IBMX and 0.8 mM ascorbic acid

Test Example 1

Evaluation of Positive allosteric modulating action (PAM action)

The PAM action of the compound of the present invention was evaluated by the ratio of a left shift of a dopamine dose response curve.

The left shift means that the dopamine dose response curve, in which the logarithm of dose is set to abscissa (X axis) and the response (in this test, cAMP concentration) is set to ordinate (Y axis), is parallely shifted in the negative direction of the X axis by the addition of PAM.

(Establishment of Human Dopamine D1 Receptor Stably-Expressing Cell)

The coding sequence of a human dopamine D1 receptor (Accession No.: NM_000794.3) was amplified by PCR, and was subcloned into a pEF-BOS vector. The obtained construct was transfected into a CHO (dhfr-) cell (ATCC No.: CRL-9096) using Lipofectamine 2000 (manufactured by Thermo Fisher Scientific Inc., Lipofectamine is a registered trademark). The stably transfected clone was obtained by the selection using 100 nM MTX. The obtained cell clone was maintained in αMEM containing 10% FBS, penicillin and streptomycin.

(Test Method)

(1) Dose-response curve of dopamine to which the compound of the present invention was added The dose-response curve of dopamine to which a test drug was added was created by performing the following experiment.

The serially diluted solution of the test drug was prepared using the buffer solution for assay (concentration 0.49 µM to 40 µM, 3-fold dilution). The above serially diluted solution of the test drug was dispensed into a black 384 well plate (Corning Inc.) by 2.5 µL.

Human dopamine D1 receptor stably-expressing CHO cells were seeded in each well at a density of about 5000 cells per well by 5 µL, were spun down by a centrifuge for plate (05PR-22, Hitachi Koki Co., Ltd., 800 rpm), and were then left to stand for 10 minutes.

The serially diluted solution of dopamine was prepared by diluting a DMSO solution of dopamine (Sigma-Aldrich Co. LLC) with the buffer solution (concentration 0.018 µM to 13.3 µM, 3-fold dilution). The above serially diluted solution of dopamine was dispensed into each well of the plate by 2.5 µL.

The plate was stirred using a plate shaker (mx-5, Sanko Junyaku Co., Ltd.), and was then left to stand for 15 minutes to 20 minutes at room temperature (final concentration: test drug 0 µM to 10 µM, dopamine 0 µM to 3.3 µM, 3-fold dilution).

To measure cAMP, LANCE Ultra cAMP kit (PerkinElmer Inc., LANCE is a registered trademark) was used. Kit reagent Eu-cAMP tracer solution and kit reagent ULight-anti-cAMP solution (ULight is a registered trademark) were respectively added to each well of the aforementioned plate in the amount of 5 µL, and the reaction was stopped. The plate was incubated at room temperature for 1 hour and then the fluorescence intensity at 665 nm and 620 nm was measured (excitation wavelength: 320 nm, fluorescence wavelength: 665 nm, 620 nm) by TR-FRET method using a plate reader (2103 Multilabel Plate Reader (registered trademark Envision), PerkinElmer, Inc.). The fluorescence intensity ratio [(fluorescence intensity at 665 nm)/(fluorescence intensity at 620 nm)×$10^4$] of each well was calculated, and was used for analysis.

As a control group, a well, to which dopamine is not added, was set to 0%, and a well, in which final concentration of dopamine is 3.3 µM, was set to 100%.

(2) Dose-Response Curve for Dopamine

The dose-response curve of dopamine was created by performing an experiment without a test drug in the same manner as in (1).

(Evaluation of Activity)

From the results of the test, it was found that the dose-response curve (1) of dopamine to which the Example compound of the present invention was added was shifted leftward based on the dose-response curve (2) of dopamine. Further, it was found that each shift value was calculated by changing the concentration of the test drug, and thus the dose-response curve of dopamine was shifted leftward in a dose-dependent manner.

Here, in the case where the dose of dopamine was 0, the test drug did not exhibit an agonistic effect.

As described above, it was found that the compound of example of the present invention has a PAM action.

The results of the compounds of some representative Example compounds of the present invention are shown in Table 1.

The value of activity was expressed by a Shift value used as an index of activity.

The shift value is a value indicating to what extent the $EC_{50}$ value of dopamine in 1.1 µM the test drug increased on the basis of the $EC_{50}$ value of dopamine without adding the test drug [Shift value=($EC_{50}$ value of dopamine without adding the test drug)/($EC_{50}$ value of dopamine in 1.1 µM the test drug)]. Therefore, if the value of the test drug is greater than 1, it is indicated that the dose-response curve of dopamine was shifted leftward by the addition of the test drug. The $EC_{50}$ value of dopamine was calculated using the dose-response curve of each dopamine.

In Table, No. represents compound number, Ex represents Example compound number, and Dat1 represents shift value.

TABLE 1

| No. | Dat1 |
|---|---|
| Ex1 | 7.3 |
| Ex2 | 2.3 |
| Ex3 | 2.0 |
| Ex4 | 2.0 |
| Ex5 | 3.6 |
| Ex6 | 2.0 |
| Ex7 | 6.2 |

Here, $EC_{50}$ 2-fold potentiation of Ex1 was 0.061 µM. The $EC_{50}$ 2-fold potentiation means test drug concentration by which the $EC_{50}$ in the dose-response curve (2) of dopamine is potentiated in 2-fold. For example, this is test drug concentration which enhance the $EC_{50}$ in the dose-response curve (2) of dopamine from 1.0 µM to 0.5 µM (2 fold, in other words, half as numerical value).

Test Example 2

Y-Maze Test

The improvement effect on cognitive impairment of the compound of the present invention was evaluated using Y-maze test that is an experimental system of spontaneous alternation behavior.

(Experimental Apparatus)

As the Y-maze, a maze in which three runways, each having a length of 40 cm, a height of 13 cm, a floor width of 3 cm, and an upper portion width of 10 cm, are attached to each other in a Y shape at an angle of 120°, was used.

(Test Method)

The single oral administration of a test drug (0.01, 0.03, 0.1 and 0.3 mg/kg, suspended in 0.5% methylcellulose) into a 5- to 6-week-old ddY male mouse (n=8 Japan SLC, Inc.) was performed in 1 hour before the start of the Y-maze test, and the intraperitoneal administration of MK-801 (Sigma-Aldrich Co. LLC), which is an NMDA receptor antagonist causing cognitive impairment, into the mouse in a dose of 0.15 mg/kg was performed in 20 minutes before the start of the Y-maze test.

Here, in the mouse of a control group, a vehicle (0.5% methylcellulose) was used instead of the test drug. Moreover, a physiological saline instead of MK-801 was used.

In the mouse of a MK-801 control group, a vehicle (0.5% methylcellulose) was used instead of the test drug.

After the aforementioned mouse was placed at the end of any runway in the Y-maze, the mouse was freely searched for eight minutes. The number of times the mouse has entered the runway was counted, and this counted number of times was set to the total entry number. The number of times the mouse has continuously entered three different runways (for example, when three arms were represented by a, b, and c, respectively, in the case where the order of entry of runways is abccbacab, it was counted by 4) was set to spontaneous alternation behavior number. Spontaneous alternation behavior rate is calculated by Calculation Equation: Spontaneous alternation behavior rate=[spontaneous alternation behavior number/(total entry number−2)]×100. The calculated spontaneous alternation behavior rate was set to an index of spontaneous alternation behavior. It is indicated that as this index value becomes higher, short-term memory is maintained.

(Data Analysis)

The measured value was represented by average value f standard error for each group. The assay of significant difference between the control group and the MK-801 control group was carried out by the Student's t-test. Further, the assay of significant difference between the test drug administration group and the MK-801 control group was carried out by the Dunnett's type multiple comparison test to determine the learning disorder improvement effect of the test drug. With P<0.05 in each assay, it was determined that the significant difference exists.

The results of significantly improving the spontaneous alternation behavior of the compounds of some representative examples of the present invention are shown in the table below. In the table, No. represents compound number, Ex represents Example compound number, and Dat2 represents minimum effective dose.

TABLE 2

| No. | Dat2 |
| --- | --- |
| Ex1 | 0.03 mg/kg |

Test Example 3

Attentional Set-Shifting Task

The compound of the present invention was evaluated by an attentional set-shifting task test.

The attentional set-shifting task test, as in WCST, is a test for measuring flexibility with respect to the change of a rule (clue). The effect on executive function disorder which is one of higher brain dysfunctions can be evaluated by this test.

After allowing the mouse to learn a task that food reward is obtained if there is a clue, in the case where the clue is shifted within a dimension (for example, the clue is changed from a form to another form), both normal animal and pathological animal having abnormality in the prefrontal cortex of the brain (hereinafter, referred to as "pathological animal") can discriminate clues to obtain food reward. However, after allowing the mouse to learn a task of obtaining food reward by a clue, in the case where the clue is shifted to the outside of a dimension (for example, the clue is changed from a form to aroma), the normal animal can discriminate a clue of food, but the pathological animal cannot discriminate the clue of food. This test puts this behavior to practical use.

The following experiments were carried out with reference to European Journal of Neuroscience, 2005, vol. 21, p. 1070-1076, which was partially modified.

(Test Method)

1. Test Apparatus and Animal

As the test apparatus, a field including a start area and a choice area partitioned by a guillotine door was used. The choice area is partially partitioned such that left and right areas have the same size, as seen from the start area. Containers filled with contents were placed in the left and right areas one by one, and food reward (cereal pieces, General Mill Inc.) was buried therein. The left and right containers were replaced at random for each test (from start to correct answer or incorrect answer in the test). Rats placed in the start area were moved to the choice area when the guillotine door was opened, and were able to act freely between the left and right areas of the choice area.

As the pathological model, rats administered with sub-chronic PCP were used. 5-week-old male Long Evans rats (Japan SLC, Inc.) were prepared by intraperitoneally administering 2 mg/mL/kg of a PCP saline for 7 days twice a day. Tests were carried out after a washout period of 7 or 8 days. Food consumption was limited during the washout period.

2. Habituation

Rats were returned to the start area after starting the test by opening the guillotine door and allowing the rats to act freely for 4 minutes. Then, containers were placed in the left and right areas of the choice area one by one, respectively. Each of the containers was filled with alpha dry (Shepherd Specialty Papers, alpha dry is a registered trademark), one of the total of two food rewards was placed at the top of each of the containers, and the other one thereof was placed at the bottom of each of the containers. The rats were returned to a home cage after starting the test and confirming that the rats completely ate the food rewards (four food rewards).

3. Training

On the same day as the habituation, a simple discrimination (SD1) task was carried out as training. One container was filled with plastic beads, and the edge thereof was coated with nutmeg aroma oil. The other container was filled with wooden beads, and the edge thereof was coated with lemon aroma oil. The food reward was placed only in the former container, and the test was started. Rats returned to the start area (1) after completely eating the food reward as a correct answer or (2) immediately after digging the container as an incorrect answer. The rats were trained until they continuously provide correct answers five times.

4. Test

On the next day of the training, the rats were allowed to search the food reward by using contents or aroma as a clue. Six discrimination tasks, relating to a combination of contents and aroma, were conducted. It was allowed to proceed to the next tasks, when each discrimination task was correctly answered continuously five times. The test was carried out in order from the first item (SD2) to the sixth item (EDR). After the completion of CD, the single oral administration of a test drug (0.001, 0.003 and 0.01 mg/kg, suspended in 0.5% methylcellulose) into the rats was carried out. In the rats of the control group, a vehicle (0.5% methylcellulose) was administered instead of the test drug.

Table 3 shows combinations of content and aroma in each task. Table 4 shows specific examples (an example). In Tables, underlines shows correct answers (clue of the container to which the food reward was placed).

TABLE 3

| | | Combinations of content and aroma |
| --- | --- | --- |
| 1 | SD2 | Corn chips or wood chips/None |
| 2 | CD | Corn chips or wooden chips/mint or ginger |
| 3 | ID | Pebbles or marbles/cinnamon or orange |
| 4 | IDR | Pebbles or marbles/cinnamon or orange |
| 5 | ED | Plastic beads or cut paper/jasmine or vanilla |
| 6 | EDR | Plastic beads or cut paper/jasmine or vanilla |

TABLE 4

| | | Left choice area (content/aroma) | Right choice area (content/aroma) |
| --- | --- | --- | --- |
| 1 | SD2 | Corn chips/none | Wooden chips/none |
| 2 | CD | Wooden chips/mint | Corn chips/ginger |
| 3 | ID | Pebbles/cinnamon | Marbles/orange |
| 4 | IDR | Pebbles/cinnamon | Marbles/orange |

TABLE 4-continued

| | | Left choice area (content/aroma) | Right choice area (content/aroma) |
|---|---|---|---|
| 5 | ED | Plastic beads/jasmine | Cut paper/vanilla |
| 6 | EDR | Plastic beads/jasmine | Cut paper/vanilla |

5. Results

The number of examples is 6 examples in each group. The statistical analysis about the number of attempts to obtain continuous correct answers five times was carried out. The Student's t-test for the control group and the PCP control group was carried out. The significant difference ($P<0.05$) was observed only in the ED, and the executive function disorder in the PCP control group was detected. Further, the Dunnett's type multiple comparison test about the test drug administration group and the PCP control group was carried out to determine the effect of improving the executive function disorder of the test drug. The significant difference was not observed from the first item (SD2) to the fourth item (IDR) of the discrimination task, and in the sixth item (EDR) thereof, and the significant difference ($P<0.05$) was observed only in the fifth item (ED) of the discrimination task.

The drug dosage at the time of the compound of representative example of the present invention improving the executive function disorder is shown in the table below. Ex represents the compound number of example. Dat3 represents a minimum effective dose.

TABLE 5

| No. | Dat3 |
|---|---|
| Ex1 | 0.003 mg/kg |

From the above test results, the compound of the present invention is expected to be used in the prevention and/or treatment of cognitive impairment, schizophrenia negative symptom, CIAS, Parkinson's disease, Alzheimer's disease, Huntington's disease, depression, ADHD, or drug dependency.

The pharmaceutical composition containing one or two or more of the compound of the formula (I) or salt thereof as an active ingredient can be prepared by a generally used method using an excipient generally used in the related art, that is, a pharmaceutical excipient or a pharmaceutical carrier.

The administration may be any form of oral administration using tablets, pills, capsules, granules, powders, or solutions, and parenteral administration using intra-articular, intravenous or intramuscular injections, suppositories, eye drops, eye ointments, transdermal liquids, ointments, transdermal patches, transmucosal solutions, transmucosal patches, or inhalants.

As the solid composition for oral administration, tablets, powders, granules, and the like are used. In this solid composition, one or two or more active ingredients are mixed with at least one inert excipient. The composition may contain inert additives, such as a lubricant, a disintegrating agent, a stabilizing agent, and a solubilizing agent according to a general method. The tablet or pill, if necessary, may be coated with a film made of sugar or a gastric or enteric substance.

The liquid composition for oral administration contains a pharmaceutically acceptable emulsion, solution, suspension, syrup, or elixir, and contain a generally used inert diluent, such as purified water or EtOH. The liquid composition may contain an adjuvant, such as a solubilizing agent, a wetting agent or a suspending agent, a sweetening agent, a flavoring agent, an aromatic agent, or an antiseptic agent in addition to the inert diluent.

The injection for parenteral administration contains a sterile aqueous or non-aqueous solution, suspension or opalizer. As the aqueous solvent, for example, distilled water for injection or a physiological saline is included. Examples of the non-aqueous solvent include alcohols, such as EtOH. Such a composition may further contain a tonicity agent, an antiseptic agent, a wetting agent, an emulsifying agent, a dispersing agent, a stabilizing agent, or a solubilizing agent. They are sterilized by the filtration through a bacteria-retaining filter, the combination of germicides, or the irradiation of light. Further, they can also be used in the form of being dissolved or suspended in sterile water or a sterile solvent for injection before they are prepared into a sterile solid composition and then used.

The external preparation includes ointment, plaster, cream, jelly, poultice, spray, lotion, eye drop, and eye ointment. The external preparation contains generally used ointment base, lotion base, aqueous or non-aqueous solution, suspension, emulsion, or the like.

The transmucosal agent, such as an inhalant or a nasal preparation, is used in the state of liquid or semi-solid, and can be prepared according to a conventionally known method. For example, a known excipient, or a pH adjuster, an antiseptic, a surfactant, a lubricant, a stabilizer, or a thickener may be suitably added. In the administration, a device for appropriate inhalation or insufflation can be used. For example, a compound can be administered in the form of powder alone or powder of a formulated mixture or in the form of solution or suspension of a combination of pharmaceutically acceptable carriers using a known device or sprayer, such as a measuring administration inhalation device. The dry powder inhaler may be used for single or multiple administration, and a dry powder or a powder-containing capsule can be used. Alternatively, the appropriate propellant, for example, may be in the form of a pressurized aerosol spray or the like using a suitable gas such as chlorofluoroalkane or carbon dioxide.

In the case of general oral administration, the daily dose is about 0.001 mg/kg to 100 mg/kg per weight, and preferably 0.0001 mg/kg to 0.01 mg/kg per weight, and is administered once or separately 2 to 4 times. In the case of intravenous administration, the daily dose is about 0.0001 mg/kg to 10 mg/kg per weight, and is administered once or separately several times in a day. In the case of a transmucosal agent, about 0.001 mg/kg to 100 mg/kg per weight is administered once or separately several times in a day. The dose is appropriately determined in consideration of symptom, age, sex, or the like depending on the individual case.

Although varied depending on administration route, dosage form, administration site, or the kind of excipients or additives, the pharmaceutical composition of the present invention contains one or more compounds of the formula (I) and salts thereof in the amount of 0.01% by weight to 100% by weight, and 0.01% by weight to 50% by weight in an aspect, as active ingredients.

The compound of the formula (I) can be used in combination with various therapeutic agents or prophylactic agents for diseases considered that the aforementioned compound of the formula (I) exhibits efficacy. The corresponding combination use may be simultaneous administration, separately continuous administration, or administration at desired time intervals. The formulation for simultaneous administration may be a combination drug, and may also be formulated separately.

EXAMPLES

Hereinafter, a method of preparing a compound of the formula (I) will be described in detail with reference to Examples. However, the present invention is not limited to the compounds described in the following examples. The production processes of starting compounds are shown in Preparation Examples. Further, the method of preparing a compound of the formula (I) is not limited only to the preparation methods of specific examples shown below, and the compound of the formula (I) may be prepared by a combination of these preparation methods or by methods obvious to those skilled in the art.

In Examples, Preparation Examples, and Tables below, the following abbreviations can be used.

Pr=Preparation Example number, Ex=Example number, Syn=Preparation method (the corresponding compound represent a compound prepared in the same method as the preparation method of the compound of Example number or Preparation Example number described in this column), Str=Structural Formula, Dat=physiochemical data, ESI+ =m/z value (represents $(M+H)^+$ unless otherwise specified) in ESI-MS, ESI-=m/z value (represents $(M-H)^-$ unless otherwise specified) in ESI-MS, NMR1=$\delta$(ppm) in $^1$H-NMR of 500 MHz in DMSO-$d_6$, and NMR2=$\delta$(ppm) in $^1$H-NMR of 400 MHz in DMSO-$d_6$. There is a case where the peak area (integral value) of chemical shift ($\delta$) of NMR is represented by a fraction by the conformation isomerism of a compound. For example, in Ex1, 7/5H represents a peak area of fifth part of 7H.

For example, in Ex2, the phrase Ex1 of Syn shows that the Example compound of Ex2, which is a target, is prepared in the same method as in the method described in Ex1. Further, it is shown that HCl in Structural Formula is hydrochloride.

2$\theta$(°) represents the diffraction angle of characteristic peaks in powder X-ray diffraction. The powder X-ray diffraction was measured using RINT-TTR II (RIGAKU Inc.) under conditions of tube: Cu, tube current: 300 mA, tube voltage: 50 kV, sampling width: 0.020°, scanning speed: 4°/min, wavelength: 1.54056 Å, measuring diffraction angle range (2$\theta$): 2.5° to 40°.

For convenience, concentration mol/L is represented as M. For example, it means that a 1M NaOH aqueous solution is a NaOH aqueous solution of 1 mol/L.

Preparation Example 1

To a mixture of NaOH (5 g), water (7 mL), TBAB (50 mg), and DMF (25 mL) was added 1-(4-phenyl-1H-imidazol-2-yl)methanamine monohydrochloride (1 g) under ice cooling, and a DMF (25 mL) solution of 1,3-dibromopropane (1.98 g) was further added thereto slowly, followed by stirring overnight at room temperature. Thereafter, an insoluble material was removed by filtration, washing with toluene was carried, and the filtrate was concentrated under reduced pressure. The residue was purified by silica gel CC (MeOH-chloroform) to obtain 2-phenyl-6,7,8,9-tetrahydro-5H-imidazo[1,2-a][1,4]diazepine (200 mg).

Preparation Example 2

To a mixture of NaOH (1.1 g), water (2 mL), TBAB (15 mg), and DMF (5 mL) was added 1-(4-phenyl-1H-imidazol-2-yl)methanamine monohydrochloride (300 mg) under ice cooling, followed by stirring for 10 minutes at the same temperature. A DMF (5 mL) solution of 2-(chloromethyl)oxirane (230 µL) was further added thereto, followed by stirring for 18 hours at room temperature and for 5 hours at 40° C. Thereafter, an insoluble material was removed by filtration, washing with toluene was carried, and the filtrate was concentrated under reduced pressure. The residue was purified by silica gel CC (MeOH-chloroform) to obtain 2-phenyl-6,7,8,9-tetrahydro-5H-imidazo[1,2-a][1,4]diazepin-6-ol (85.3 mg).

Preparation Example 3

To a mixture of NaOH (1.0 g), water (3 mL), TBAB (17 mg), and DMF (10 mL) was added 1-[4-(4-fluorophenyl)-1H-imidazol-2-yl)methanamine dihydrochloride (446 mg) under ice cooling, followed by stirring for 10 minutes at the same temperature. A DMF (10 mL) solution of 1-bromo-3-chloropropane (250 µL) was further added thereto, followed by stirring for 1 hour at room temperature and overnight at 50° C. Thereafter, an insoluble material was removed by filtration, washing with toluene was carried, and the filtrate was concentrated under reduced pressure. The residue was purified by silica gel CC (MeOH-chloroform), so as to obtain 2-(4-fluorophenyl)-6,7,8,9-tetrahydro-5H-imidazo[1,2-a][1,4]diazepine (20.8 mg).

Preparation Example 4

To a DMF (45 mL) solution of ({4-[4-(trifluoromethyl)phenyl]-1H-imidazol-2-yl}methyl)carbamic acid tert-butyl ester (3 g) were added 1-bromo-3-chloropropane (0.95 mL) and $K_2CO_3$ (3.64 g), followed by stirring overnight at 60° C. Thereafter, the reaction solution was filtered by celite, and solids were washed with DMF (15 mL). To the filtrate was added KOtBu (1.97 g) under ice cooling, followed by stirring for 2 hours at the same temperature under an argon atmosphere. Thereafter, water was added to the reaction solution, followed by extraction with EtOAc, and the organic layer was washed with water and brine in this order, dried over $MgSO_4$, and then concentrated under reduced pressure. The residue was purified by silica gel CC (EtOAc-hexane) to obtain 2-[4-(trifluoromethyl)phenyl]-6,7-dihydro-5H-imidazo[1,2-a][1,4]diazepine-8(9H)-carboxylic acid tert-butyl ester (1.26 g).

Preparation Example 5

To an acetic acid (9 mL) solution of 4-benzyl-1-(5-fluoro-2-nitrophenyl)-1,4-diazepan-2-one (440 mg) was added iron (286 mg), followed by stirring for 3 hours at 80° C. Thereafter, the reaction solution was filtered by celite, the filtrate was diluted with EtOAc, and the organic layer was washed with saturated aqueous sodium bicarbonate and brine in this order, dried over $MgSO_4$, and then concentrated under reduced pressure. The residue was purified by silica gel CC (EtOAc-hexane) to obtain 2-benzyl-8-fluoro-2,3,4,5-tetrahydro-1H-[1,4]diazepino[1,2-a]benzimidazole (150 mg).

Preparation Example 6

To a dioxane (15 mL) solution of 4-benzyl-1,4-diazepan-2-one (500 mg) were added 2-bromo-4-fluoro-1-nitrobenzene (538 mg), Pd2dba3 (67 mg), xantphos (127 mg), and $Cs_2CO_3$ (1 g), followed by stirring overnight at 100° C.

under an argon atmosphere. Thereafter, dilution with EtOAc was carried out, and the organic layer was washed with water and brine in this order, dried over $Na_2SO_4$, and then concentrated under reduced pressure. The residue was purified by silica gel CC (EtOAc-hexane) to obtain 4-benzyl-1-(5-fluoro-2-nitrophenyl)-1,4-diazepan-2-one (440 mg).

Preparation Example 7

To a toluene (30 mL) solution of [(tert-butoxycarbonyl)amino] acetic acid 2-oxo-2-[4-(trifluoromethyl)phenyl]ethyl ester (3 g) was added ammonium acetate (3.2 g), followed by reflux overnight. Thereafter, water was added to the reaction solution, followed by extraction with EtOAc. The organic layer was washed with brine, dried over $Na_2SO_4$, and then concentrated under reduced pressure. The residue was purified by silica gel CC (EtOAc-hexane) to obtain ({4-[4-(trifluoromethyl)phenyl]-1H-imidazol-2-yl}methyl) carbamic acid tert-butyl ester (2.6 g).

Preparation Example 8

To a MeCN (60 mL) solution of N-(tert-butoxycarbonyl)glycine (3 g) were added 2-bromo-1-[4-(trifluoromethyl)phenyl]ethanone (4.57 g) and $K_2CO_3$ (2.4 g), followed by stirring for 1 hour at room temperature. Thereafter, the reaction solution was filtered by celite, and the filtrate was concentrated under reduced pressure to obtain [(tert-butoxycarbonyl)amino]acetic acid 2-oxo-2-[4-(trifluoromethyl)phenyl]ethyl ester (6 g).

Preparation Example 9

To a dichloromethane (12.5 mL) solution of 2-[4-(trifluoromethyl)phenyl]-6,7-dihydro-5H-imidazo[1,2-a][1,4]diazepine-8(9H)-carboxylic acid tert-butyl ester (1.25 g) was added a 4M hydrogen chloride/dioxane solution (4.1 mL), followed by stirring overnight at room temperature. Thereafter, concentration under reduced pressure was carried out to obtain 2-[4-(trifluoromethyl)phenyl]-6,7,8,9-tetrahydro-5H-imidazo[1,2-a][1,4]diazepine hydrochloride (1.1 g).

Preparation Example 10

To an EtOH (5.5 mL) solution of 2-benzyl-8-fluoro-2,3,4,5-tetrahydro-1H-[1,4]diazepino[1,2-a]benzimidazole (140 mg) was added 10% Pd/C (50 mg), followed by stirring overnight under a hydrogen atmosphere. Thereafter, the reaction solution was filtered by celite, and the filtrate was concentrated under reduced pressure to obtain 8-fluoro-2,3,4,5-tetrahydro-1H-[1,4]diazepino[1,2-a]benzimidazole (97 mg).

Preparation Example 11

To a mixture of 2-amino-3,4-difluorophenol (6.9 g) and dioxane (70 mL) was added CDI (10 g) at room temperature, followed by stirring for 2 hours at 60° C. Thereafter, a 1 M hydrochloric acid aqueous solution was added to the reaction mixture, followed by dilution with EtOAc, and the organic layer was washed with brine, dried over $Na_2SO_4$, and then concentrated under reduced pressure. The residue was purified by silica gel CC (EtOAc-hexane) to obtain 4,5-difluoro-1,3-benzoxazol-2(3H)-one (3.65 g).

Preparation Example 12

To a mixture of 4,5-difluoro-1,3-benzoxazol-2(3H)-one (100 mg) and MeCN (2 mL) were added $K_2CO_3$ (105 mg) and bromoacetic acid tert-butyl ester (100 µL) at room temperature, followed by stirring for 2.5 hours at 50° C. Thereafter, EtOAc was added to the reaction mixture, the solid was collected by filtration, followed by washing with EtOAc and drying under reduced pressure. The residue was purified by silica gel CC (EtOAc-hexane) to obtain (4,5-difluoro-2-oxo-1,3-benzoxazol-3(2H)-yl)acetic acid tert-butyl ester (180 mg).

Preparation Example 13

To a mixture of 4-fluoro-1,3-benzoxazol-2(3H)-one (27.2 g) and MeCN (500 mL) were added $K_2CO_3$ (35.2 g) and bromoacetic acid tert-butyl ester (27.6 mL) at room temperature, followed by stirring overnight at 60° C. The reaction mixture was cooled to room temperature, an insoluble material was separated by filtration, and the filtrate was concentrated under reduced pressure. A mixed solvent of hexane-EtOAc (9:1) was added to the resulting residue and then the obtained solid was collected by filtration, followed by washing with the mixed solvent of hexane-EtOAc (9:1) to obtain (4-fluoro-2-oxo-1,3-benzoxazol-3(2H)-yl)acetic acid tert-butyl ester (42.6 g).

Preparation Example 14

To a dichloromethane (2 mL) solution of (4,5-difluoro-2-oxo-1,3-benzoxazol-3(2H)-yl)acetic acid tert-butyl ester (166 mg) was added TFA (400 µL) at room temperature, followed by stirring for 3 hours at the same temperature. The reaction mixture was concentrated under reduced pressure, and hexane was added thereto. A solid was collected by filtration, washed with hexane, and dried under reduced pressure to obtain (4,5-difluoro-2-oxo-1,3-benzoxazol-3(2H)-yl) acetic acid (128 mg).

Preparation Example 15

To a mixture of (4-fluoro-2-oxo-1,3-benzoxazol-3(2H)-yl)acetic acid tert-butyl ester (5 g) and dichloromethane (14 mL) was added TFA (7 mL) at room temperature, followed by stirring overnight at the same temperature. The reaction mixture was concentrated under reduced pressure, and the obtained solid was collected by filtration, washed with diethyl ether, and dried under reduced pressure to obtain (4-fluoro-2-oxo-1,3-benzoxazol-3(2H)-yl)acetic acid (3.65 g).

Preparation Example 16

To a mixture of (4,5-difluoro-2-oxo-1,3-benzoxazol-3(2H)-yl)acetic acid (80 mg) and dichloromethane (1 mL) were added HATU (140 mg) and DIPEA (120 µL), and a mixture of 2-phenyl-6,7,8,9-tetrahydro-5H-imidazo[1,2-a][1,4]diazepin-6-ol (80 mg) and dichloromethane (2 mL) was added thereto, followed by stirring for 2 hours at room temperature. The reaction solution was diluted with chloroform, and saturated aqueous sodium bicarbonate was added thereto. The obtained solid was collected by filtration, and washed with water and chloroform to obtain 4,5-difluoro-3-[2-(6-hydroxy-2-phenyl-6,7-dihydro-5H-imidazo[1,2-a][1,4]diazepin-8(9H)-yl)-2-oxoethyl]-1,3-benzoxazol-2(3H)-one (64 mg). The filtrate was washed with water and brine in this order, and then dried over $Na_2SO_4$ and concentrated under reduced pressure. The residue was purified by silica gel CC (MeOH-chloroform) to obtain 4,5-difluoro-3-[2-(6- hydroxy-2-phenyl-6,7-dihydro-5H-imidazo[1,2-a][1,4]diazepin-8(9H)-yl)-2-oxoethyl]-1,3-benzoxazol-2(3H)-one (9.7 mg).

Example 1

To a mixture of (4-fluoro-2-oxo-1,3-benzoxazol-3(2H)-yl)acetic acid (656 mg) and dichloromethane (20 mL) were added HATU (1.29 g) and DIPEA (1.9 mL), followed by stirring for 3 minutes at room temperature. Next, 2-[4-(trifluoromethyl)phenyl]-6,7,8,9-tetrahydro-5H-imidazo[1,2-a][1,4]diazepine hydrochloride (1 g) was added thereto, followed by stirring overnight at room temperature. After the reaction solution was diluted with EtOAc, the organic layer was washed with water, saturated aqueous sodium bicarbonate and brine in this order, and then dried over MgSO₄ and concentrated under reduced pressure. The residue was purified by silica gel CC (MeOH-chloroform), and further purified by silica gel CC (EtOAc-hexane) to obtain 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one (1.1 g).

The 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one prepared by the above method was crystallized by the following crystallization of (1) or (2).

(1) An EtOH (1.6 mL) solution of 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one (230 mg) was stirred for 3 hours at room temperature. The deposited precipitate was collected by filtration and dried under reduced pressure to obtain A01 crystal (A01 form) of 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one (51 mg).

(2) An EtOH (80 mL) solution of 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one (39.5 g) was stirred for 30 minutes at room temperature. Thereafter, the solid obtained by slowly carrying out concentration under reduced pressure was dried to obtain A02 crystal (A02 form) of 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one (36 g).

Example 11

To a dichloromethane (10 mL) solution of (5-chloro-2-oxo-1,3-benzoxazol-3(2H)-yl)acetic acid (230 mg) were added 2,3,4,5-tetrahydro-1H-[1,4]diazepino[1,2-a]benzimidazole (160 mg), WSC.HCl (220 mg), and HOBt (105 mg), followed by stirring for 12 hours at room temperature. Water was added to the reaction solution, followed by extraction with chloroform. The organic layer was washed with brine, and then dried over Na₂SO₄ and concentrated under reduced pressure. The residue was purified by silica gel CC (MeOH-chloroform), and then the obtained crude product was solidified with EtOAc-hexane to obtain 5-chloro-3-[2-(4,5-dihydro-1H-[1,4]diazepino[1,2-a]benzimidazol-2(3H)-yl)-2-oxoethyl]-1,3-benzoxazol-2(3H)-one (70 mg).

Example 12

To a dichloromethane (15 mL) solution of (5-chloro-2-oxo-1,3-benzoxazol-3(2H)-yl)acetic acid (530 mg) were added oxalyl chloride (1.18 g) and a catalytic amount of DMF under ice cooling, followed by stirring for 3 hours at room temperature. The reaction solution was concentrated under reduced pressure, the residue was dissolved in dichloromethane (15 mL), 8,9-dimethyl-2,3,4,5-tetrahydro-1H-[1,4]diazepino[1,2-a]benzimidazole (400 mg) and TEA (1.6 mL) were added under ice cooling, followed by stirring for 12 hours at room temperature. Thereafter, the reaction solution was concentrated under reduced pressure, and the residue was purified by silica gel CC (MeOH-chloroform) and solidified with EtOAc-hexane to obtain 5-chloro-3-[2-(8,9-dimethyl-4,5-dihydro-1H-[1,4]diazepino[1,2-a]benzimidazol-2(3H)-yl)-2-oxoethyl]-1,3-benzoxazol-2(3H)-one (453 mg).

Examples 13 and 14

To a mixture of dichloromethane (1 mL) and 4,5-difluoro-3-[2-(6-hydroxy-2-phenyl-6,7-dihydro-5H-imidazo[1,2-a][1,4]diazepin-8(9H)-yl)-2-oxoethyl]-1,3-benzoxazol-2(3H)-one (40 mg) was added bis(2-methoxyethyl)aminosulfur trifluoride (80 μL) under ice cooling, followed by stirring for 2 hours at the same temperature and for 19 hours at room temperature. Water was added to the reaction solution, followed by extraction with chloroform. The organic layer was washed with brine, and then dried over Na₂SO₄ and concentrated under reduced pressure. The residue was purified by silica gel CC (MeOH-chloroform) to obtain 4,5-difluoro-3-[2-(6-fluoro-2-phenyl-6,7-dihydro-5H-imidazo[1,2-a][1,4]diazepin-8(9H)-yl)-2-oxoethyl-1,3-benzoxazol-2(3H)-one (11.1 mg) and 4,5-difluoro-3-[2-oxo-2-(2-phenyl-7H-imidazo[1,2-a][1,4]diazepin-8(9H)-yl)ethyl]-1,3-benzoxazol-2(3H)-one (17.3 mg).

TABLE 6

| No. | Str |
| --- | --- |
| Pr1 | |
| Pr1-1 | |
| Pr2 | |
| Pr3 | |
| Pr3-1 | |

TABLE 6-continued
| No. | Str |
|---|---|
| Pr3-2 | 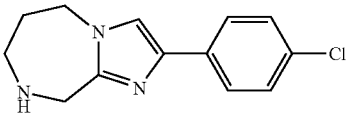 |
| Pr3-3 | 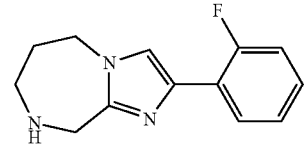 [SMILES: Fc1ccccc1-c1cn2c(n1)CNCCC2] |
| Pr4 | 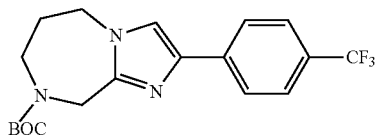 [SMILES: CC(C)(C)OC(=O)N1CCCn2cc(-c3ccc(C(F)(F)F)cc3)nc2C1] |
| Pr5 | 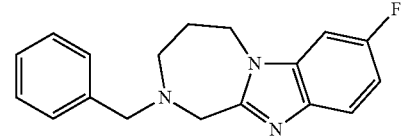 [SMILES: Fc1ccc2nc3n(c2c1)CCCN(Cc1ccccc1)C3] |
| Pr6 | 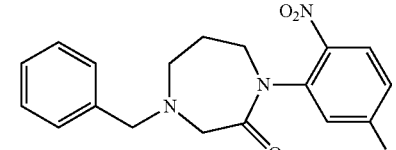 |
| Pr7 | 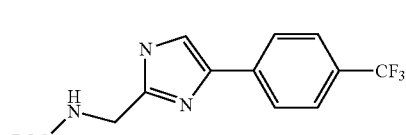 |
| Pr7-1 | 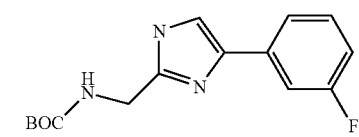 |
| Pr7-2 | 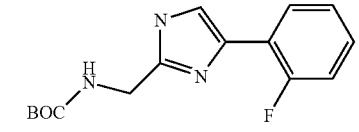 [SMILES: CC(C)(C)OC(=O)NCc1nc(-c2ccccc2F)c[nH]1] |
| Pr8 | 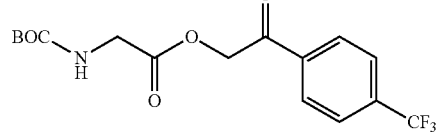 |
| Pr8-1 | 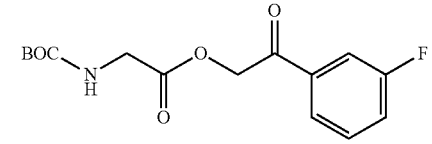 [SMILES: CC(C)(C)OC(=O)NCC(=O)OCC(=O)c1cccc(F)c1] |
| Pr8-2 | 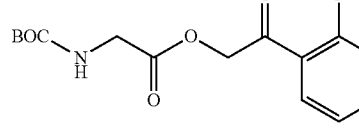 |
TABLE 7
| No. | Str |
|---|---|
| Pr9 | 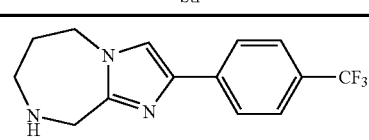 |
| Pr9-1 | 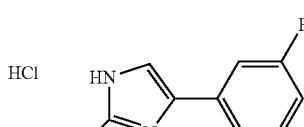 |
| Pr9-2 | 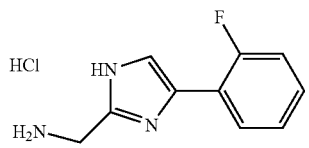 [SMILES: Cl ; NCc1nc(-c2ccccc2F)c[nH]1] |
| Pr10 | 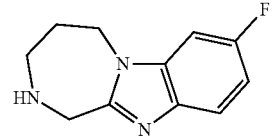 [SMILES: Fc1ccc2nc3n(c2c1)CCCNC3] |
| Pr11 | 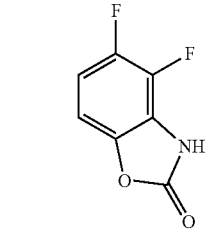 [SMILES: O=c1[nH]c2c(F)c(F)ccc2o1] |
| Pr12 | 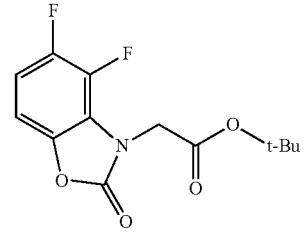 [SMILES: CC(C)(C)OC(=O)Cn1c(=O)oc2ccc(F)c(F)c21] |
| Pr13 | 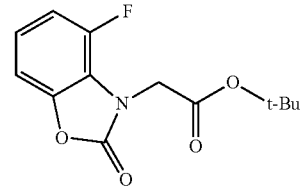 [SMILES: CC(C)(C)OC(=O)Cn1c(=O)oc2cccc(F)c21] |

TABLE 7-continued
| No. | Str |
|---|---|
| Pr14 | 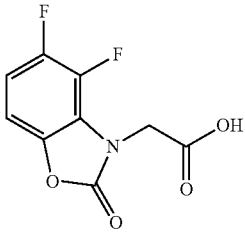 [SMILES: O=C(O)Cn1c(=O)oc2ccc(F)c(F)c21] |
| Pr15 | 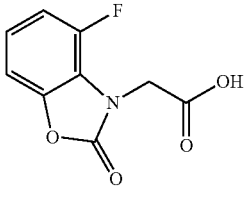 [SMILES: O=C(O)Cn1c(=O)oc2cccc(F)c21] |
TABLE 8
| No. | Str |
|---|---|
| Pr16 | 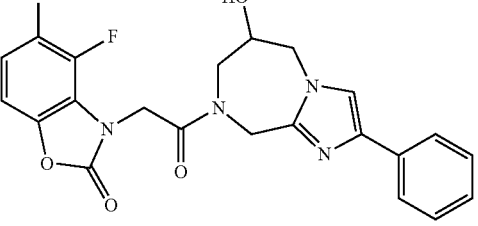 |
| Ex1 | 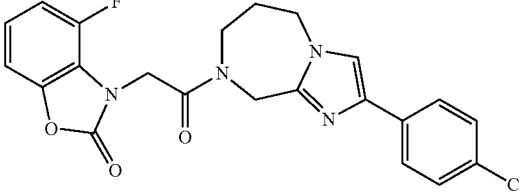 |
| Ex2 | 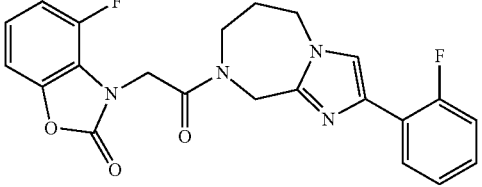 |
| Ex3 | 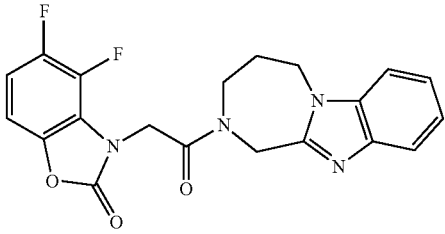 [SMILES: O=C(Cn1c(=O)oc2ccc(F)c(F)c21)N1CCCn2c(nc3ccccc32)C1] |
| Ex4 | 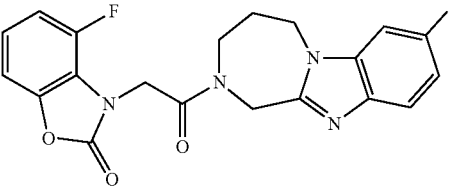 |
| Ex5 | 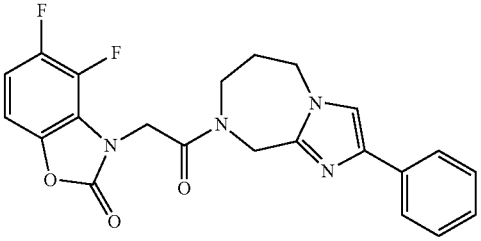 [SMILES: O=C(Cn1c(=O)oc2ccc(F)c(F)c21)N1CCCn2cc(-c3ccccc3)nc2C1] |
| Ex6 | 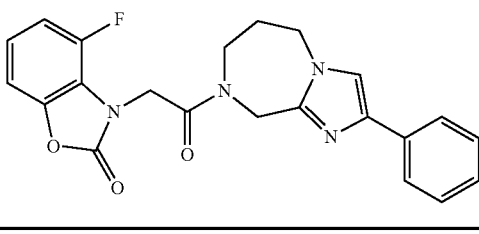 |
TABLE 9
| No. | Str |
|---|---|
| Ex7 | 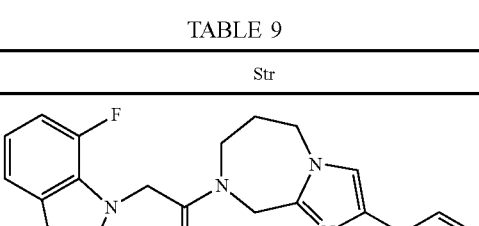 |
| Ex8 | 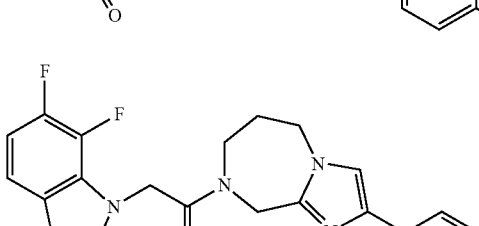 |
| Ex9 | 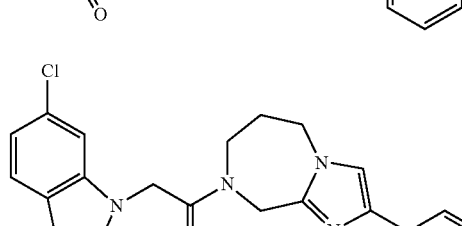 |

TABLE 9-continued

| No. | Str |
|---|---|
| Ex10 | 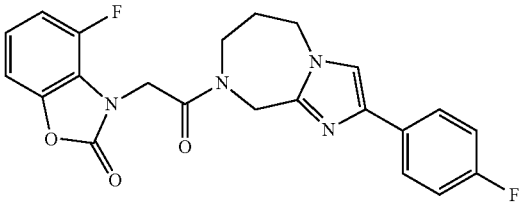 [SMILES: O=C(Cn1c(=O)oc2cccc(F)c21)N1CCCn2cc(-c3ccc(F)cc3)nc2C1] |
| Ex11 | 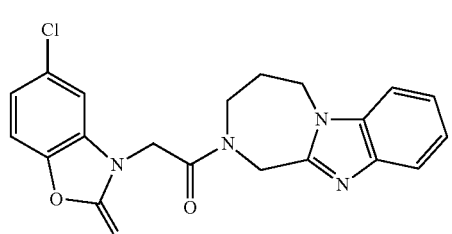 |
| Ex12 | 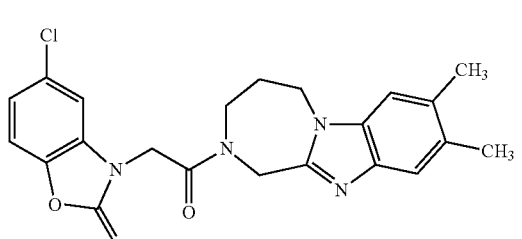 |

TABLE 10

| No. | Str |
|---|---|
| Ex13 | 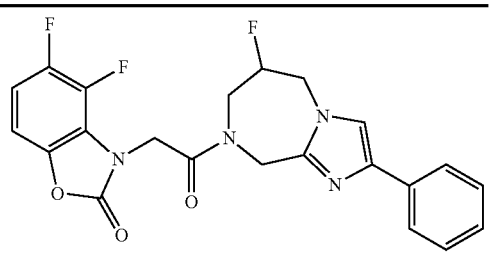 |
| Ex14 | 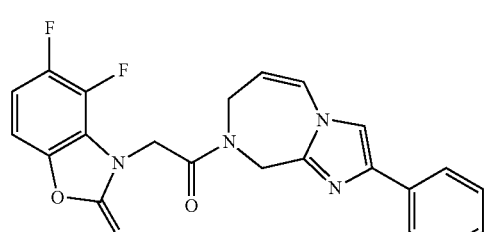 |

TABLE 11

| No. | Syn | Dat |
|---|---|---|
| Pr1 | Pr1 | ESI+: 214 |
| Pr1-1 | Pr1 | ESI+: 216 |
| Pr2 | Pr2 | ESI+: 230 |
| Pr3 | Pr3 | ESI+: 232 |
| Pr3-1 | Pr3 | ESI+: 232 |
| Pr3-2 | Pr3 | ESI+: 248 |
| Pr3-3 | Pr3 | ESI+: 232 |
| Pr4 | Pr4 | ESI+: 382 |
| Pr5 | Pr5 | ESI+: 296 |
| Pr6 | Pr6 | ESI+: 344 |
| Pr7 | Pr7 | ESI+: 342 |
| Pr7-1 | Pr7 | ESI+: 292 |
| Pr7-2 | Pr7 | ESI+: 292 |
| Pr8 | Pr8 | ESI−: 360[M − H]− |
| Pr8-1 | Pr8 | ESI+: 334[M + Na]+ |
| Pr8-2 | Pr8 | ESI+: 334[M + Na]+ |
| Pr9 | Pr9 | ESI+: 282 |
| Pr9-1 | Pr9 | ESI+: 192 |
| Pr9-2 | Pr9 | ESI+: 192 |
| Pr10 | Pr10 | ESI+: 206 |
| Pr11 | Pr11 | ESI−: 170[M − H]− |
| Pr12 | Pr12 | ESI+: 308[M + Na]+ |
| Pr13 | Pr13 | ESI+: 290[M + Na]+ |
| Pr14 | Pr14 | ESI+: 230 |
| Pr15 | Pr15 | ESI+: 212 |
| Pr16 | Pr16 | ESI+: 441 |

TABLE 12

| No. | Syn | Dat |
|---|---|---|
| Ex1 | Ex1 | ESI+: 475<br>NMR1(ppm): 1.77-1.85(m, 7/5H), 2.02-2.09(m, 3/5H), 3.77-3.92(m, 2H), 4.23-4.35(m, 2H), 4.71-5.08(m, 4H), 6.96-7.16(m, 2H), 7.19-7.28(m, 1H), 7.65-7.72(m, 2H), 7.81-7.95(m, 3H).<br>A01 form: 2Θ(°) = 6.7, 13.6, 15.2, 15.6, 18.5, 19.4, 20.4, 23.3, 25.5, 26.6.<br>A02 form: 2Θ(°) = 7.0, 9.4, 12.3, 15.8, 17.4, 18.9, 19.6, 21.3, 23.8, 25.0. |
| Ex2 | Ex1 | ESI+: 425<br>NMR1(ppm): 1.75-1.83(m, 7/5H), 1.99-2.06(m, 3/5H), 3.77-3.91(m, 2H), 4.27-4.36(m, 2H), 4.73-5.05(m, 4H), 6.96-7.15(m, 2H), 7.20-7.27(m, 4H), 7.51-7.60(m, 1H), 7.94-8.07(m, 1H). |
| Ex3 | Ex1 | ESI+: 399<br>NMR2(ppm): 1.82-1.91(m, 7/5H), 2.08-2.16(m, 3/5H), 3.85-3.98(m, 2H), 4.41-4.51(m, 2H), 4.92(s, 3/5H), 4.96(s, 3/5H), 5.06(s, 14/5H), 7.09-7.31(m, 4H), 7.53-7.66(m, 2H). |
| Ex4 | Ex1 | ESI+: 399<br>NMR2(ppm): 1.80-1.89(m, 7/5H), 2.06-2.15(m, 3/5H), 3.83-3.98(m, 2H), 4.38-4.50(m, 2H), 4.86-5.08(m, 4H), 6.91-7.27(m, 4H), 7.49-7.67(m, 2H). |
| Ex5 | Ex1 | ESI+: 425<br>NMR2(ppm): 1.76-1.84(m, 7/5H), 2.00-2.08(m, 3/5H), 3.77-3.90(m, 2H), 4.20-4.29(m, 2H), 4.71-5.07(m, 4H), 7.10-7.38(m, 5H), 7.56-7.75(m, 3H). |
| Ex6 | Ex1 | ESI+: 425 |
| Ex7 | Ex1 | ESI+: 441 |
| Ex8 | Ex1 | ESI+: 443 |
| Ex9 | Ex1 | ESI+: 423 |
| Ex10 | Ex1 | ESI+: 425 |
| Ex11 | Ex11 | ESI+: 397 |
| Ex12 | Ex12 | ESI+: 425 |
| Ex13 | Ex13, Ex14 | ESI+: 443 |
| Ex14 | Ex13, Ex14 | ESI+: 423 |

INDUSTRIAL APPLICABILITY

A compound of the formula (I) or a salt thereof has a PAM action on a dopamine D1 receptor, and is expected as an agent for preventing and/or treating cognitive impairment, schizophrenia negative symptom, CIAS, Parkinson's disease, Alzheimer's disease, Huntington's disease, depression, ADHD, drug dependency, or the like.

The invention claimed is:

1. A compound of the formula (I) or a salt thereof:

$$\text{(I)}$$

wherein:
R$^1$, R$^2$, and R$^3$ are the same as or different from each other, and are H, halogen, lower alkyl, or halo-lower alkyl;
R$^4$ is H, halogen, lower alkyl, or halo-lower alkyl;
R$^5$ is H;
R$^6$ is phenyl which can be substituted; or
R$^5$ and R$^6$ can form a benzene ring which can be substituted, together with carbon atoms to which they are bonded; and
═══ is a single bond or a double bond.

2. The compound or a salt thereof according to claim 1, wherein R$^5$ is H, and R$^6$ is phenyl which can be substituted.

3. The compound or a salt thereof according to claim 2, wherein ═══ is a single bond.

4. The compound or a salt thereof according to claim 3, wherein R$^4$ is H.

5. The compound or a salt thereof according to claim 4, wherein R$^1$ is H, R$^2$ is H or halogen, and R$^3$ is halogen.

6. The compound or a salt thereof according to claim 5, wherein R$^6$ is phenyl which can be substituted with one to four R$^{41}$'s which are the same as or different from each other, and
R$^{41}$ is a group selected from the group consisting of —OH, —O-lower alkyl, —CN, halogen, lower alkyl, halo-lower alkyl, lower alkylene-O-lower alkyl, —C(═O)-lower alkyl, and —C(═O)-lower alkylene-CN.

7. The compound or a salt thereof according to claim 6, wherein R$^6$ is phenyl which can be substituted with one R$^{42}$, and
R$^{42}$ is a group selected from the group consisting of halogen, lower alkyl, and halo-lower alkyl.

8. The compound or a salt thereof according to claim 7, wherein R$^2$ is H.

9. The compound or a salt thereof according to claim 8, wherein R$^6$ is phenyl which can be substituted with one R$^{42}$ at a para-position from its bond.

10. A compound or a salt thereof which is selected from the group consisting of:
4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one,
4-fluoro-3-{2-[2-(2-fluorophenyl)-6,7-dihydro-5H-imidazo[1,2-a][1,4]diazepin-8(9H)-yl]-2-oxoethyl}-1,3-benzoxazol-2(3H)-one,
3-[2-(4,5-dihydro-1H-[1,4]diazepino[1,2-a]benzimidazol-2(3H)-yl)-2-oxoethyl]-4,5-difluoro-1,3-benzoxazol-2(3H)-one,
4-fluoro-3-[2-(8-fluoro-4,5-dihydro-1H-[1,4]diazepino[1,2-a]benzimidazol-2(3H)-yl)-2-oxoethyl]-1,3-benzoxazol-2(3H)-one,
4,5-difluoro-3-[2-oxo-2-(2-phenyl-6,7-dihydro-5H-imidazo[1,2-a][1,4]diazepin-8(9H)-yl)ethyl]-1,3-benzoxazol-2(3H)-one,
4-fluoro-3-{2-[2-(3-fluorophenyl)-6,7-dihydro-5H-imidazo[1,2-a][1,4]diazepin-8(9H)-yl]-2-oxoethyl}-1,3-benzoxazol-2(3H)-one, and
3-{2-[2-(4-chlorophenyl)-6,7-dihydro-5H-imidazo[1,2-a][1,4]diazepin-8(9H)-yl]-2-oxoethyl}-4-fluoro-1,3-benzoxazol-2(3H)-one.

11. The compound or a salt thereof according to claim 10, wherein the compound is selected from the group consisting of:
4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one,
4-fluoro-3-{2-[2-(2-fluorophenyl)-6,7-dihydro-5H-imidazo[1,2-a][1,4]diazepin-8(9H)-yl]-2-oxoethyl}-1,3-benzoxazol-2(3H)-one,
4,5-difluoro-3-[2-oxo-2-(2-phenyl-6,7-dihydro-5H-imidazo[1,2-a][1,4]diazepin-8(9H)-yl)ethyl]-1,3-benzoxazol-2(3H)-one,
4-fluoro-3-{2-[2-(3-fluorophenyl)-6,7-dihydro-5H-imidazo[1,2-a][1,4]diazepin-8(9H)-yl]-2-oxoethyl}-1,3-benzoxazol-2(3H)-one, and
3-{2-[2-(4-chlorophenyl)-6,7-dihydro-5H-imidazo[1,2-a][1,4]diazepin-8(9H)-yl]-2-oxoethyl}-4-fluoro-1,3-benzoxazol-2(3H)-one.

12. The compound or a salt thereof according to claim 10, wherein the compound is 4-fluoro-3-(2-oxo-2-{2-[4-(trifluoromethyl)phenyl]-6,7-dihydro-5H-imidazo[1,2-a][1,4]diazepin-8(9H)-yl}ethyl)-1,3-benzoxazol-2(3H)-one.

13. The compound or a salt thereof according to claim 10, wherein the compound is 3-{2-[2-(4-chlorophenyl)-6,7-dihydro-5H-imidazo[1,2-a][1,4]diazepin-8(9H)-yl]-2-oxoethyl}-4-fluoro-1,3-benzoxazol-2(3H)-one.

14. A pharmaceutical composition, comprising a compound or a salt thereof according to claim 1 and a pharmaceutically acceptable excipient.

15. A method for treating cognitive impairment, schizophrenia negative symptom, cognitive impairment associated with schizophrenia (CIAS), Parkinson's disease, Huntington's disease, depression, or attention deficit hyperactivity disorder (ADHD), which comprises administering an effective amount of the compound or a salt thereof according to claim 10 to a subject in need thereof.

16. A pharmaceutical composition, comprising a compound or a salt thereof according to claim 2 and a pharmaceutically acceptable excipient.

17. A pharmaceutical composition, comprising a compound or a salt thereof according to claim 3 and a pharmaceutically acceptable excipient.

18. A pharmaceutical composition, comprising a compound or a salt thereof according to claim 4 and a pharmaceutically acceptable excipient.

19. A pharmaceutical composition, comprising a compound or a salt thereof according to claim 5 and a pharmaceutically acceptable excipient.

20. A method for treating cognitive impairment, schizophrenia negative symptom, cognitive impairment associated with schizophrenia (CIAS), Parkinson's disease, Huntington's disease, depression, or attention deficit hyperactivity disorder (ADHD), which comprises administering an effective amount of the compound or a salt thereof according to claim 11 to a subject in need thereof.

* * * * *